United States Patent
Moskowitz et al.

(10) Patent No.: US 8,784,450 B2
(45) Date of Patent: Jul. 22, 2014

(54) INTERARTICULATING SPINOUS AND TRANSVERSE PROCESS STAPLES FOR SPINAL FUSION

(76) Inventors: Mosheh T. Moskowitz, Rockville, MD (US); Ahmnon D. Moskowitz, Rockville, MD (US); Nathan C. Moskowitz, Rockville, MD (US)

(*) Notice: Subject to any disclaimer, the term of this patent is extended or adjusted under 35 U.S.C. 154(b) by 89 days.

(21) Appl. No.: 13/101,129

(22) Filed: May 4, 2011

(65) Prior Publication Data
US 2011/0319935 A1  Dec. 29, 2011

Related U.S. Application Data

(63) Continuation-in-part of application No. 12/471,345, filed on May 22, 2009, now Pat. No. 8,257,370, and a continuation-in-part of application No. 12/471,340, filed on May 22, 2009, now abandoned, which is a continuation-in-part of application No. 12/054,335, filed on Mar. 24, 2008, now Pat. No. 7,972,363, which is a continuation-in-part of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279.

(60) Provisional application No. 60/670,231, filed on Apr. 12, 2005, provisional application No. 61/419,679, filed on Dec. 3, 2010, provisional application No. 61/425,749, filed on Dec. 21, 2010.

(51) Int. Cl.
   *A61B 17/70* (2006.01)
(52) U.S. Cl.
   USPC .......................................................... 606/247

(58) Field of Classification Search
   CPC ............. A61B 17/0642; A61B 17/068; A61B 17/7065; A61B 17/707; A61B 17/809; A61B 17/7064; A61B 17/8042; A61B 17/86; A61B 2017/0641; A61B 2017/064; A61F 2/447; A61F 2/4637; A61F 2/0643; A61F 2220/0033; A61F 2220/0025
   USPC ............. 606/70, 247, 249, 324, 279, 74, 205; 623/17.11, 17.16
   See application file for complete search history.

(56) References Cited

U.S. PATENT DOCUMENTS

| | | | | |
|---|---|---|---|---|
| 4,976,722 | A | * | 12/1990 | Failla .............................. 606/157 |
| 5,002,552 | A | * | 3/1991 | Casey ............................ 606/157 |
| 6,026,827 | A | * | 2/2000 | Revais ........................... 132/277 |
| 6,786,070 | B1 | * | 9/2004 | Dimig et al. ..................... 70/277 |
| 6,852,117 | B2 | * | 2/2005 | Orlowski ........................ 606/120 |
| 8,206,420 | B2 | * | 6/2012 | Patel et al. ..................... 606/249 |

(Continued)

*Primary Examiner* — Pedro Philogene
(74) *Attorney, Agent, or Firm* — Dresch IP Law, PLLC; John J. Dresch

(57) ABSTRACT

Thoracic/lumbar and cervical spinous process staples which staple/fuse adjacent spinous processes are disclosed. Thoracic/lumbar transverse process staples which staple/fuse adjacent transverse processes are also disclosed. Each embodiment has upper and lower claws connected by a ratchet spring mechanism, along with a multiplicity of bone fastener prongs attached to the upper and lower claws. Two sets of prongs on each staple claw are spaced by a distance approximately equal to the distance separating adjacent spinous or transverse processes so as to facilitate stapling/fusion of two adjacent processes. Also disclosed are staple prongs with multiple perforations which enable incorporation of bone fusion material thereby facilitating stapling/fusion of spinal elements.

51 Claims, 27 Drawing Sheets

(56) References Cited

U.S. PATENT DOCUMENTS

| | | | |
|---|---|---|---|
| 8,267,300 B2 * | 9/2012 | Boudreaux | 227/175.1 |
| 2003/0216736 A1 * | 11/2003 | Robinson et al. | 606/61 |
| 2009/0054988 A1 * | 2/2009 | Hess | 623/17.16 |
| 2009/0062869 A1 * | 3/2009 | Claverie et al. | 606/324 |
| 2009/0163920 A1 * | 6/2009 | Hochschuler et al. | 606/74 |

\* cited by examiner

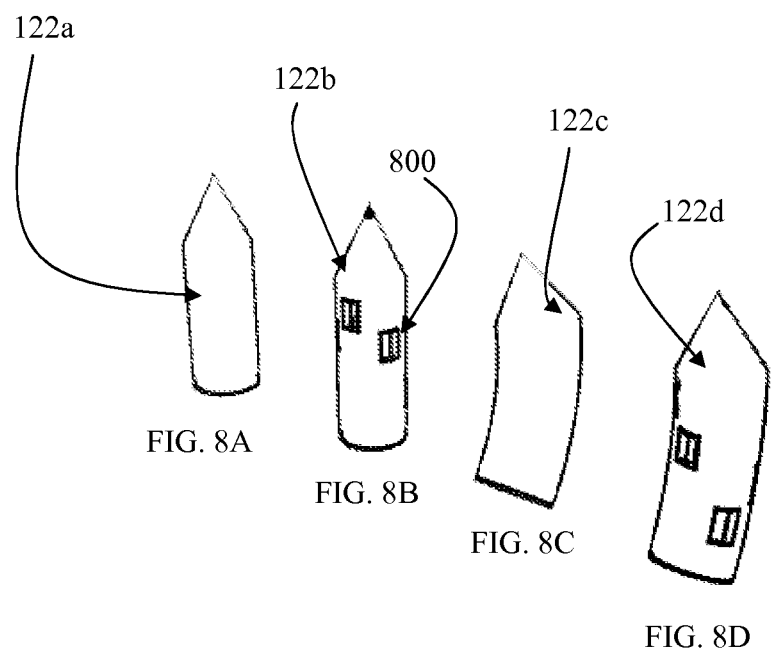

INTERARTICULATING SPINOUS AND TRANSVERSE PROCESS STAPLES FOR SPINAL FUSION

CROSS-REFERENCE TO RELATED APPLICATIONS

This application is a Continuation-In-Part Application of application Ser. No. 12/471,345, filed on May 22, 2009 (now U.S Pat. No. 8,257,370, issued on Sept. 4, 2012) and application Ser. No. 12/471,340, filed on May 22, 2009 now abandoned, each of which is a Continuation-In-Part Application of application Ser. No. 12/054,335, filed on Mar. 24, 2008 (now U.S. Pat. No. 7,972,363, issued on Jul. 5, 2011), which is a Continuation-In-Part of application Ser. No. 11/842,855, filed on Aug. 21, 2007 (now U.S. Pat. No. 7,942,903, issued on May 17, 2011), which is a Continuation-In-Part of application Ser. No. 11/536,815, filed on Sep. 29, 2006 (now U.S. Pat. No. 7,846,188; issued on Dec. 7, 2010), which is a Continuation-In-Part of application Ser. No. 11/208,644, filed on Aug. 23, 2005 (now U.S. Pat. No. 7,704,279), issued on Apr. 27, 2010 ), and this application also claims priority under 35 U.S.C. 119(e) of U.S. Provisional Application No. 60/670,231, filed on Apr. 12, 2005, U.S. Provisional Application No. 61/419,679, filed on Dec. 3, 2010, and U.S. Provisional Application No. 61/425,749, filed on Dec. 21, 2010; the entire contents of all the above identified patent applications are hereby incorporated by reference in their entirety.

This application is related to applicant's co-pending U.S. application Ser. No. 13/101,135, filed on May 4, 2011,titled "SPINOUS PROCESS STAPLE WITH INTERDIGITATING-INTERLOCKING HEMI-SPACERS FOR ADJACENT SPINOUS PROCESS SEPARATION AND DISTRACTION", which is incorporated herein by reference in its entirety.

FIELD OF DISCLOSURE

The present invention relates to stand-alone or supplemental cervical, thoracic and lumbosacral Spinous Process (SP) interarticulating staples, and thoracic/lumbosacral Transverse Process (TP) interlacing staples. Both the SP and TP interarticulating staples can be surgically implanted and function independently as stand-alone spinal segmental fusion devices and/or can be employed supplementally in tandem with each other, and/or supplementally in tandem with facet joint (FJ) interarticulating staples according to the above-referenced related applications of Applicants, and/or supplementally with other known fusion devices to achieve stable spinal fusion. The embodiments of these invention may obviate and/or lessen the need for posterior supplemental pedicle screw fixation, as well as anterior or lateral plate fixation/instrumentation, and thereby achieve a safer and more minimally invasive method of achieving spinal segmental fixation/fusion.

The present invention also relates to staple prongs with multiple perforations which allow packing of bone and/or bone growth material within the prongs thereby facilitating the integration/fusion of the device to the spine, minimizing and/or preventing implant extrusion, and promoting bone fusion.

BACKGROUND

The history and evolution of instrumented spinal fusion in the entire human spine has been reviewed in related pending application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11,536,815 filed on Sep. 29, 2006, and Ser. No. 11/208,644 filed on Aug. 23, 2005, the contents of which are hereby incorporated by reference in their entirety.

Conventionally, the majority of posterior cervical, and posterior and lateral, thoracic and lumbosacral fusion techniques, as well as anterior and/or lateral thoracic/lumbosacral fusion techniques are typically supplemented with pedicle screw placement.

Complications of pedicle screw placement in the spine include duration of procedure, significant tissue dissection and muscle retraction, misplaced screws with neural and/or vascular injury, excessive blood loss, need for transfusions, prolonged recovery, incomplete return to work, and excessive rigidity leading to adjacent segmental disease requiring further fusions and re-operations.

Recent advances in pedicle screw fixation including minimally invasive, and stereotactic CT image-guided technology, and the development of flexible rods, imperfectly address some but not all of these issues.

Complications of anterior plating/instrumentation in the anterior lumbar spine include potential devastating injury to the major vessels due to chronic vascular erosion of major vessels, or acute vascular injuries due to partial or complete plate and or screw pull-out. Recent advances including diminishing plate width and/or profile, and absorbable plates/screws, imperfectly address some, but not all of these issues.

Furthermore, for re-do surgeries, plate removal can be arduous with potential complications of vascular, and/or neural injury and screw breakage.

Lateral access to the lumbosacral spine can be complicated by damage to the genitofemoral nerve. Sensory and motor evoked potential monitoring during this surgery imperfectly address some but not all of these issues.

SUMMARY

The above-referenced related applications of Applicants describe spinal facet joint (FJ) interarticulating staples that address and attempt to improve or resolve the above problems and issues. The exemplary embodiments of the invention described herein are modifications of the facet joint (FJ) stapling device of the above-referenced related applications of Applicants and which are specifically adapted to execute adjacent spinal level Spinous Process (SP) and Transverse Process (TP) segmental fixation/fusion and which further address, improve upon, and/or resolve the above-referenced problems. The exemplary embodiments can further minimize and/or avoid transpedicular, anterior, and lateral spinal fusion instrumentation techniques and thereby avoid their concomitant complications and disadvantages which are detailed above. These exemplary embodiments continue to advance minimally invasive and low risk spinal device technology.

Herein described are multiple exemplary spinal fusion device embodiments of Spinous Process (SP) and Transverse Process (TP) interarticulating staples. These embodiments are exemplarily described for thoracic/lumbosacral SP interarticulating staples, thoracic/lumbosacral TP interarticulating staples, and cervical SP interarticulating staples.

For example, two broadly distinct SP staple embodiments are described; one for thoracic/lumbosacral SP fusion, and one for cervical SP fusion. These two distinctly designed embodiments take into account the inherent anatomical differences between cervical and lumbar SP size, geometry, topography, bone thickness and inter-spinous process distance(s).

Likewise the design of the thoracic/lumbosacral Transverse Process (TP) interarticulating staple embodiment takes into account the unique inter-TP distance(s), and the geometric contour, topography, and bone thickness of the TP compared to the SP elements.

The present disclosure recognizes the aforementioned problems with conventional apparatuses and solves these problems by, among other things, improving upon the designs illustrated in the aforementioned related applications. The present disclosure provides an advanced minimally invasive and low risk method of segmental spinal fusion via the use of interarticulating SP and TP stapling devices.

The exemplary embodiments of SP and TP fixating stapling devices described herein, and the FJ stapling device, described in the above-referenced related applications of Applicants, each can independently or in various combinations of co-supplemental application provide as strong or stronger segmental fusion as pedicle screws without the complications arising from pedicle screw placement, which include screw misplacement with potential nerve and/or vascular injury, violation of healthy facets, possible pedicle destruction, blood loss, and overly rigid fusions.

The stapling/fusion of adjacent SPs and/or TPs, and/or FJs can minimize or avoid, and hence minimize or prevent, destruction of healthy facet joints. Because the embodiments avoid fusion of anterior, middle and posterior columns, as do pedicle screws, the exemplary embodiments in essence create more flexible, i.e. less rigid, fusion, and hence diminish the possibility of adjacent level disease, and thus the probability of further operations requiring fusion extensions, i.e. re-operations.

The present disclosure recognizes that the very advantage of transpedicular screws which facilitate a strong solid fusion by rigidly engaging all three spinal columns is the same mechanical mechanism whereby complete inflexibility of all columns is incurred, thereby leading to increasing rostral and caudal segmental stress which leads to increased rates of reoperation.

The present disclosure also recognizes that SP and TP stapling/fusion whether performed via open, endoscopic, or percutaneous fluoroscopically guided surgical techniques lead to a more flexible fusion, far less muscle retraction, blood loss and significant reduction in operating room time. Thus, the complication(s) of pedicle screw pull-out, and hence the high re-operation rate associated with conventional flexible pedicle screws/rods is obviated. Although one could opt to supplement these constructs with pedicle screws, there would be no absolute need to do so with the operative devices described herein.

The exemplary embodiments for both SP and TP staples can be used to perform multiple levels of fusion engaging a series of adjacent pair of SPs and TPs with one staple per unit of two adjacent elements. These embodiments can be employed to adjoin (fuse) multiple levels of SPs and TPs in incremental spinal process units of two.

Both SP and TP staples can also be modified (elongated) to staple/fuse three or more spinal elements using a single staple.

The further advantages of SP and TP stapling throughout the spine include speed and safety. Insertion of these devices does not involve and hence does not traverse neural/vascular structures, and hence the risk of neural or vascular injury is entirely avoided.

The relative speed of insertion, and safety of these devices conferred by their capacity to be inserted via percutaneous, open, or minimally invasive techniques, with or without endoscopic or fluoroscopic guidance, minimizes overall surgical risks. Thus, the performance of SP and TP stapling/fusion is amenable to an outpatient setting which would alleviate the economic burden of spinal fusion surgery.

For example, in an exemplary embodiment, a thoracic/lumbosacral Spinous Process (SP) staple may include a top claw and a bottom claw with a plurality of ridges, a staple pin pivotally connecting the top claw and the bottom claw, and a ratchet mechanism that limits an opening force of the top claw with respect to the bottom claw. The ratchet mechanism may include a ratchet pin pivotably-mounted to the top claw, wherein the claws can include a plurality of claw teeth which interdigitate with each other, and the ratchet pin can include a flexure spring engaging the plurality of ratchet teeth. The plurality of claw ridges can help incorporate the staple into the bone.

The top and bottom claws of the staple may also include a plurality of prongs. Further, two sets of upper and lower claw prongs may be utilized to penetrate each thoracic/lumbosacral SP. The distance between the two sets of upper and lower claw prongs can be the average distance between the lumbar SPs. The two sets of upper and lower claw prongs can be manufactured with varying interspinous distances accounting for varying intra and inter-patient anatomical differences.

In an exemplary embodiment, a total of sixteen prongs may be utilized; eight prongs per SP unit. Further, a total of eight prongs on the upper claw and eight prongs on the lower jaw may be utilized; four prongs on the upper claw for penetration of each SP and four prongs on the lower claw for penetration of each SP. Upon clamping (e.g., completely clamping) the staple on two adjacent SPs, a total of eight prongs can penetrate each SP; four from the upper claw, and four from the bottom claw. The two sets of prongs per SP unit can be spaced apart on the upper and lower claws at a distance equal to the interspinous process distance such that the claws will engage and perforate each adjacent SP.

Other exemplary embodiments of staple prongs, including solid-straight, solid-curved, perforated-straight and perforated-curved are described herein and are contemplated by the present invention.

The perforated prongs may include multiple perforations within the prongs themselves which can allow the packing of autologous, or allograft bone, bone putty, bone morphogenic protein, bmp, bone marrow aspirate or any biological or synthetic material which promotes bone fusion. Further, these embodiments can facilitate integration of the device into the bone and promote bony fusion.

The exemplary embodiments having curved or straight prong(s) can be selected based on anatomical variations and surgical preference.

In another exemplary embodiment, a thoracic/lumbosacral Transverse Process (TP) staple may include a top claw and a bottom claw with a plurality of ridges, a staple pin pivotally connecting the top claw and the bottom claw, and a ratchet mechanism that limits an opening force of the top claw with respect to the bottom claw. The ratchet mechanism may include a ratchet pin pivotably mounted to the top claw. The claws may include a plurality of interdigitating claw teeth, and the ratchet pin can include a flexure spring engaging the plurality of ratchet teeth. The plurality of claw ridges can help incorporate the staple into the bone.

The top and bottom claws of the TP staple may also include a plurality of prongs. Further, there may be two sets of upper and lower claw prongs which can penetrate each TP unit. The distance between the two sets of prongs on the upper and lower claws can be the average distance between lumbar TPs. The two sets of upper and lower claw prongs can be manufactured with varying inter-TP distances accounting for varying intra and inter-patient anatomical differences. The staple claws can be contoured to hug the transverse processes and can have two sets of prongs separated by the inter-TP distance. In an embodiment, four prongs may penetrate each TP unit; two prongs can be located on the upper claw and two opposing prongs can be located on the lower claw which may engage and perforate each TP. When the staple is clamped (i.e., fully clamped or closed) on two adjacent TPs, a total of four prongs can engage each TP.

Other exemplary embodiments of staple prongs, including solid-straight, solid-curved, perforated-straight and perforated-curved are described herein and are contemplated by the present invention.

An embodiment having perforated prongs may include multiple perforations within the prongs themselves which can allow the packing of autologous, or allograft bone, bone putty, bone morphogenic protein, bmp, bone marrow aspirate or any biological or synthetic material which promotes fusion. These embodiments may facilitate integration of the device into the bone thereby facilitating bony fusion.

Embodiments having curved or straight prong(s) can be selected based on anatomical variations and surgical preference.

In another exemplary embodiment, a cervical Spinous Process (SP) staple may include a top claw and a bottom claw including a plurality of ridges, a staple pin pivotally connecting the top claw and the bottom claw, and a ratchet mechanism that can limit an opening force of the top claw with respect to the bottom claw. The ratchet mechanism may include a ratchet pin pivotably mounted to the top claw. The claws can include a plurality of claw teeth, and the ratchet pin may include a flexure spring engaging the plurality of ratchet teeth. The plurality of ridges may help incorporate the staple into the bone.

The cervical SP staple may be formed to hug the contour of the SPs. Further, the cervical SP staple can be inserted from above because of the limited interspinous distance. The two opposing proximal elements of the cervical staple may be curved to avoid depressing the tips of the spinous processes, and the claws can be contoured to be flush with any unique cervical spinous process slope and geometry.

The top and bottom claws of the cervical staple may include a plurality of prongs. The cervical staple may include two sets of upper and lower claw prongs for penetration of each cervical SP. The distance between the upper and lower sets of prongs can be the average distance between two adjacent cervical SPs, and can be manufactured with varying interspinous distances accounting for varying intra and inter-patient anatomical differences. The cervical staple may include four prongs within the staple. The cervical staple may include two sets of prongs; one set per penetration of each SP. For each set, one prong can be located on the upper claw and one prong can be located on the lower claw. When the staple is closed (i.e., clamped), two prongs may engage/penetrate each cervical SP; one from the top claw, and one from the lower claw.

Other exemplary embodiments of staple prongs, including solid-straight, solid-curved, perforated-straight and perforated-curved are described herein and are contemplated by the present invention.

The perforated prongs may include multiple perforations within the prongs themselves which can allow the packing of autologous, or allograft bone, bone putty, bone morphogenic protein, bmp, bone marrow aspirate or any biological or synthetic material which promotes fusion. These embodiments may facilitate integration of the device into the SP thereby facilitating bony fusion.

The exemplary embodiments having curved or straight prong(s) can be selected based on anatomical variations and surgical preference.

BRIEF DESCRIPTION OF THE DRAWINGS

The accompanying drawings are presented to aid in the description of embodiments of the invention and are provided solely for illustration of the embodiments and not limitation thereof.

FIG. 8A illustrates a perspective view of the straight-solid staple prong, according to an exemplary embodiment of the invention.

FIG. 8B illustrates a perspective view of the straight-perforated staple prong, according to an exemplary embodiment of the invention.

FIG. 8C illustrates a perspective view of the curved-solid staple prong, according to an exemplary embodiment of the invention.

FIG. 8D illustrates a perspective view of the curved-perforated staple prong, according to an exemplary embodiment of the invention.

DETAILED DESCRIPTION OF THE EXEMPLARY EMBODIMENTS

Figure 1A:
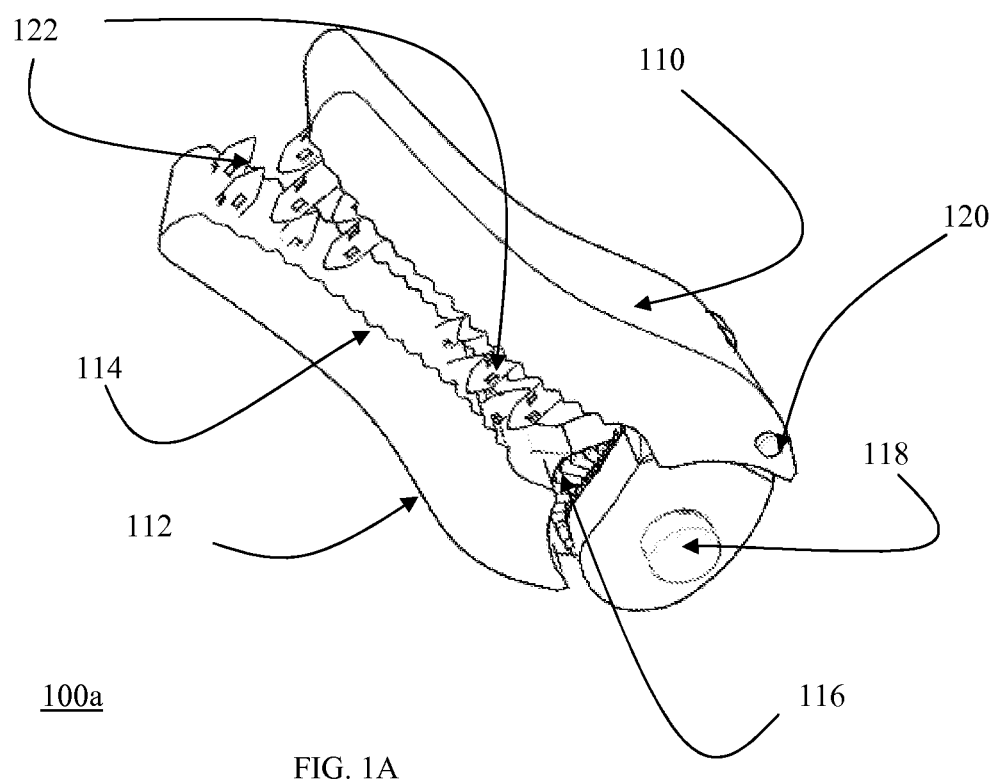
FIG. 1A illustrates a perspective (lateral) view of the thoracic/lumbosacral Spinous Process (SP) staple in a closed position, according to an exemplary embodiment of the invention.
Figure 1B:
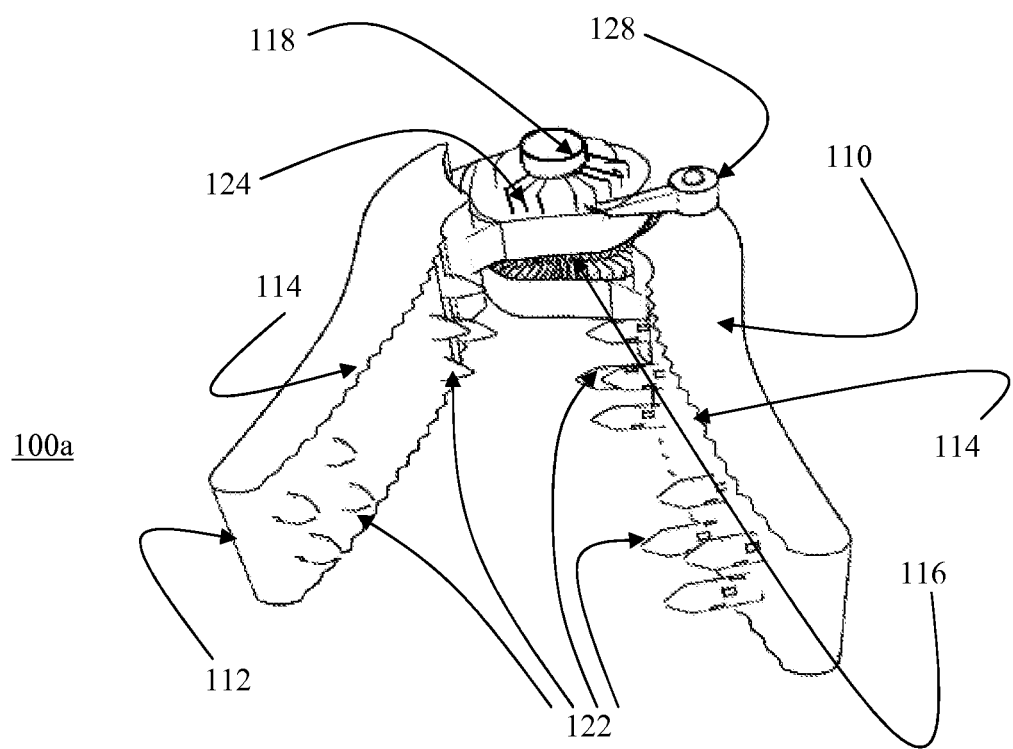
FIG. 1B illustrates a side perspective (top oblique) view of the thoracic/lumbosacral SP staple in an open position, according to an exemplary embodiment of the invention.
Figure 1C:
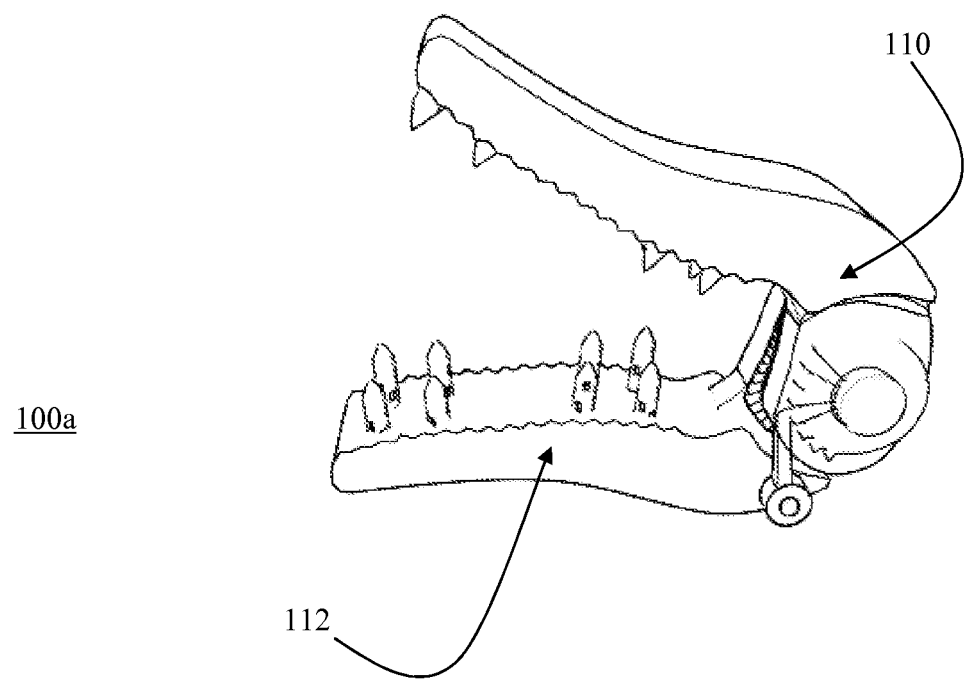
FIG. 1C illustrates a perspective (lateral) view of the thoracic/lumbosacral SP staple in an open position, according to an exemplary embodiment of the invention.
Figure 1D:
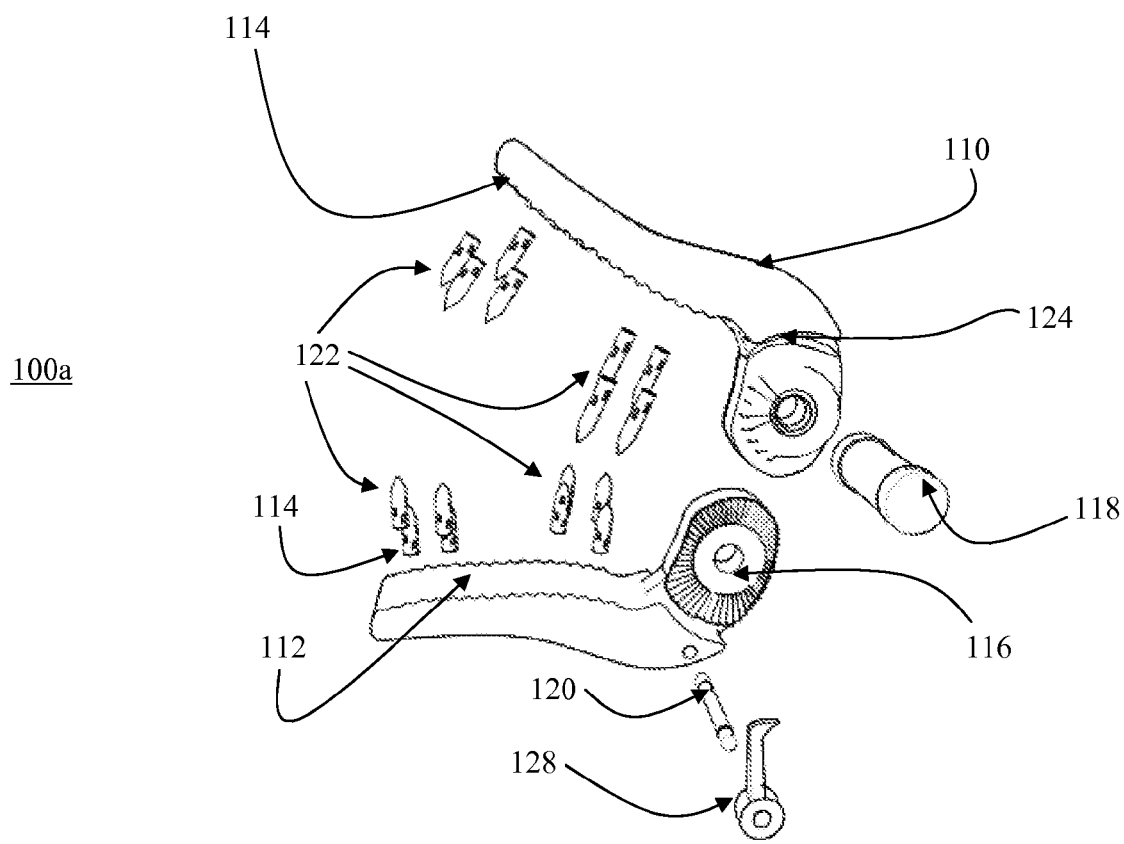
FIG. 1D illustrates an exploded view of the thoracic/lumbosacral SP staple, according to an exemplary embodiment of the invention.
Figure 2A:
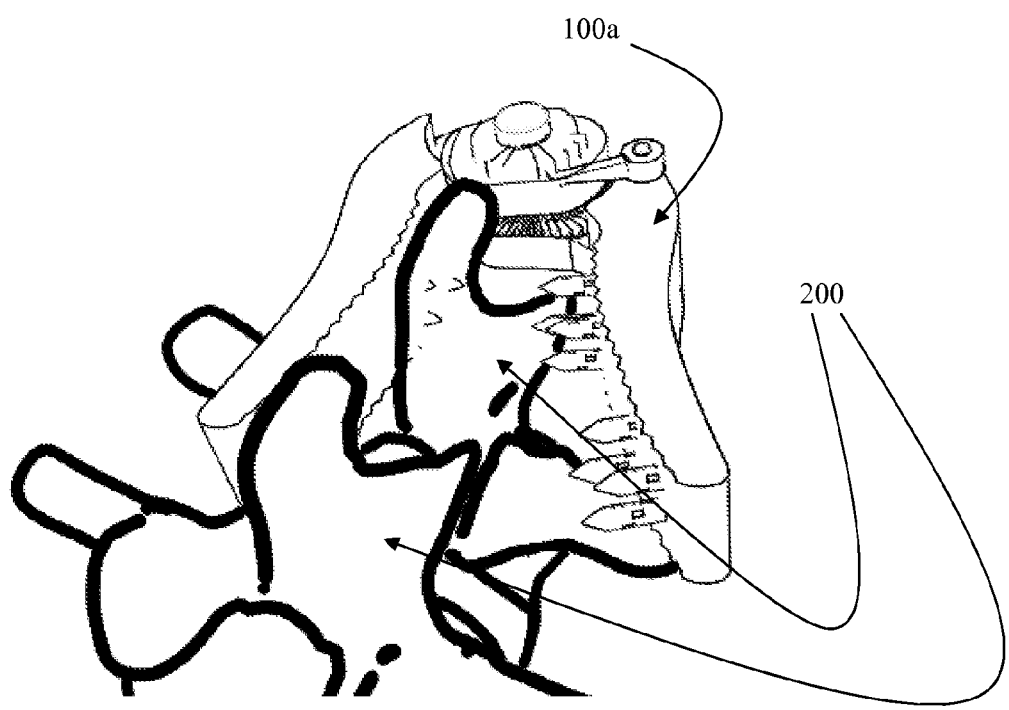
FIG. 2A illustrates a perspective (top oblique) assembly view of the lumbosacral Spinous Process (SP) staple articulating with two SPs in a partially open (partially clamped) position, according to an exemplary embodiment of the invention.
Figure 2B:
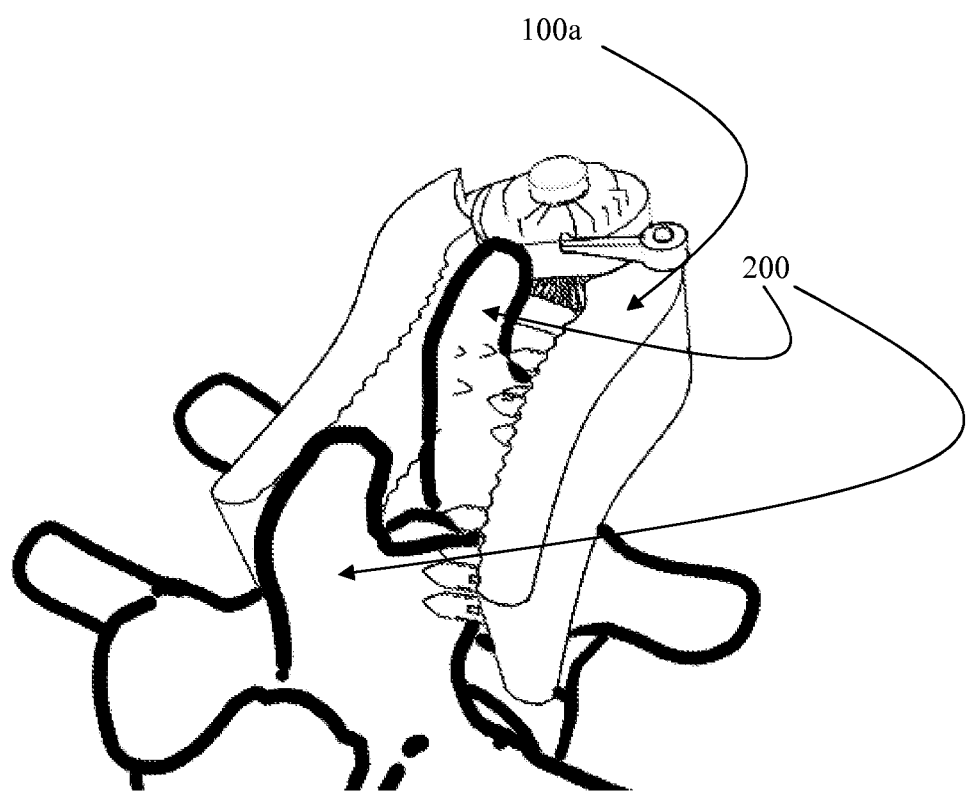
FIG. 2B illustrates a perspective (top oblique) assembly view of the lumbosacral SP staple articulating with two SPs in a partially open (partially clamped) position, according to an exemplary embodiment of the invention.
Figure 2C:
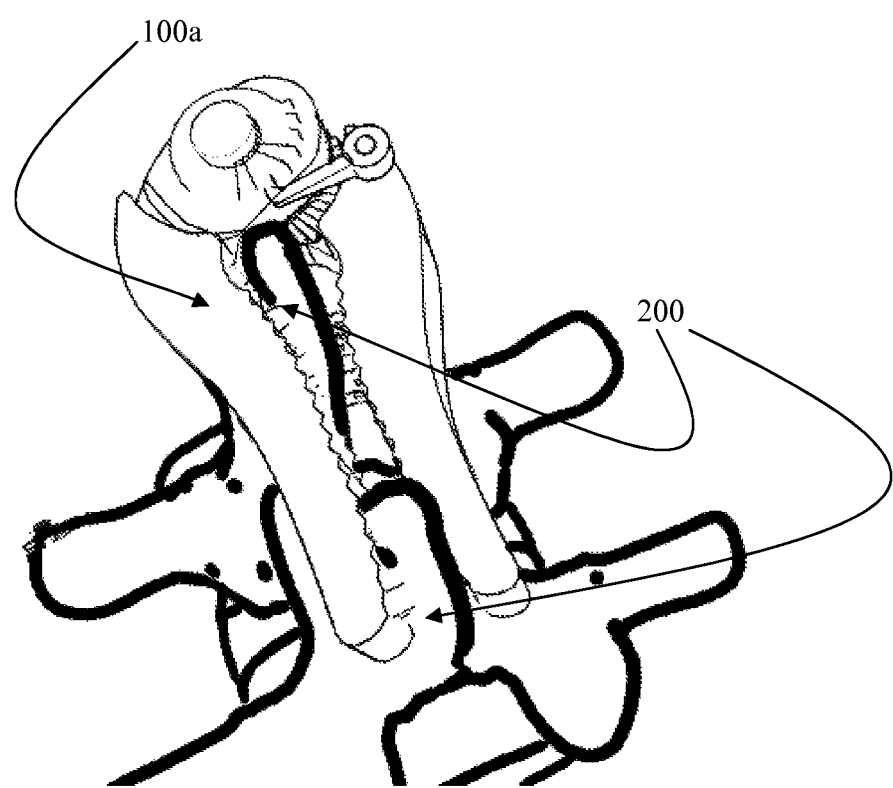
FIG. 2C illustrates a perspective (top oblique) assembly view of the lumbosacral SP staple articulating with two SPs in a closed (clamped) position, according to an exemplary embodiment of the invention.
Figure 2D:
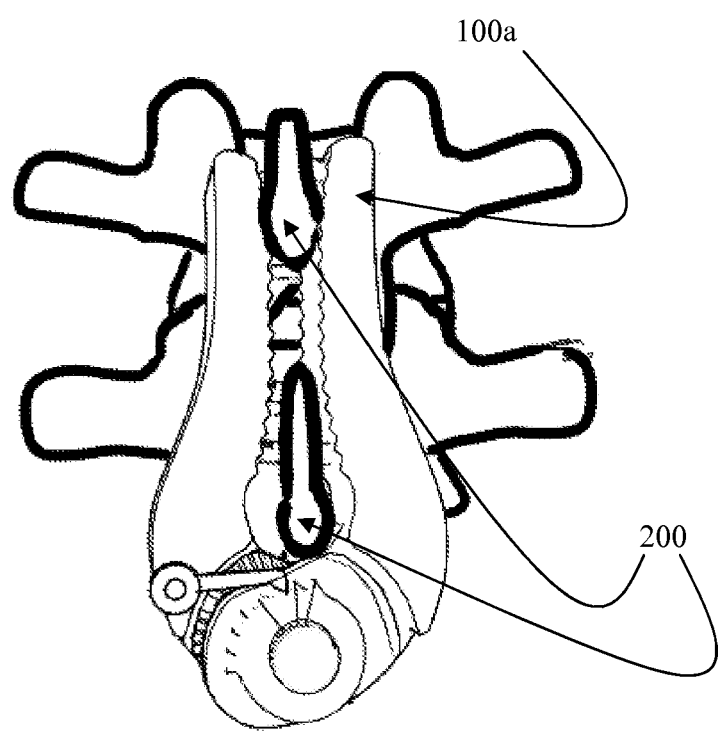
FIG. 2D illustrates a top assembly view of the lumbosacral SP staple articulating with two SPs in a closed (clamped) position, according to an exemplary embodiment of the invention.
Figure 2E:
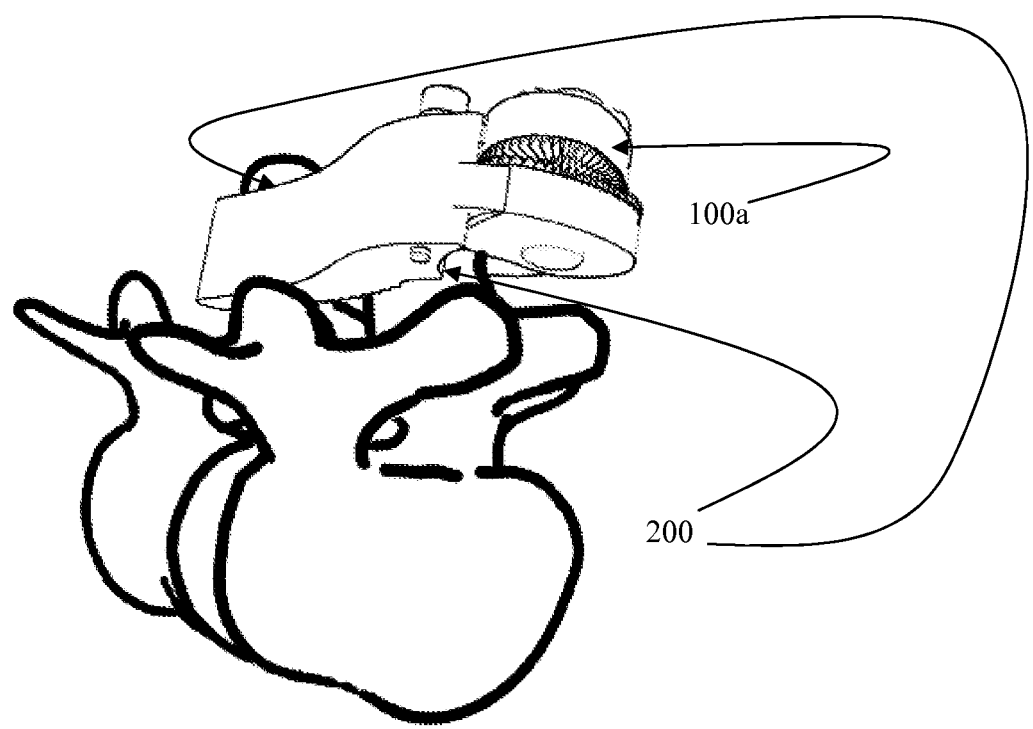
FIG. 2E illustrates a top (posterior-oblique) assembly perspective view of the lumbosacral SP staple articulating with two SPs in a closed (clamped) position, according to an exemplary embodiment of the invention.
Figure 3A:
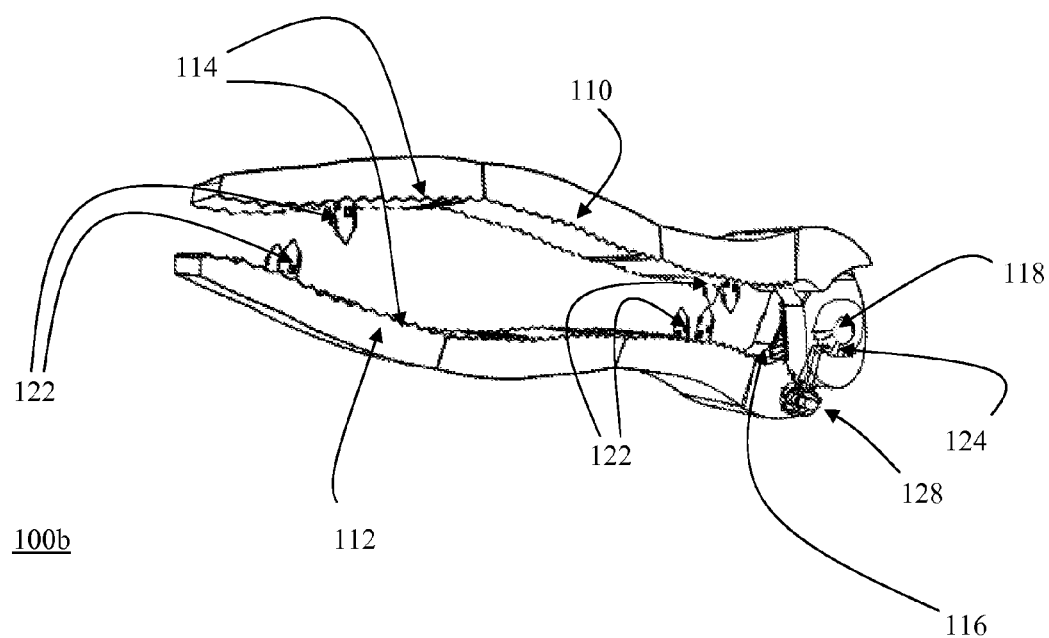
FIG. 3A illustrates a perspective (lateral) view of the thoracic/lumbosacral Transverse Process (TP) staple in a partially closed (partially clamped) position, according to an exemplary embodiment of the invention.
Figure 3B:
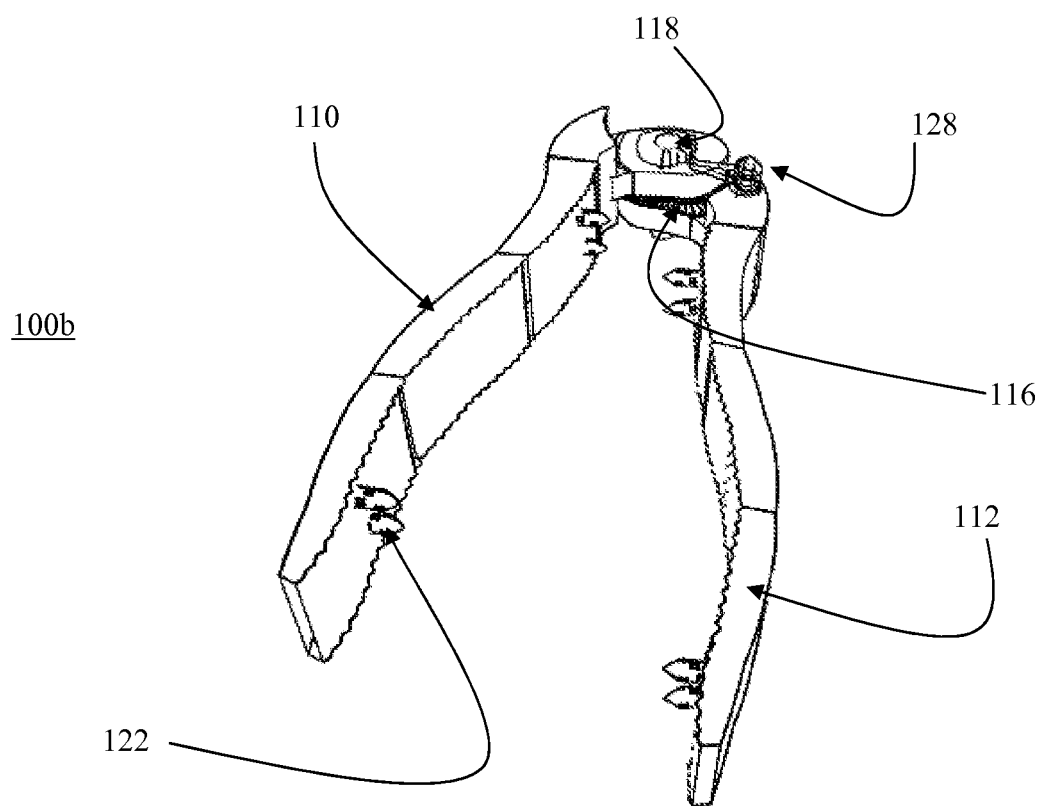
FIG. 3B illustrates a perspective (top oblique) view of the thoracic/lumbosacral TP staple in an open (unclamped) position, according to an exemplary embodiment of the invention.
Figure 3C:
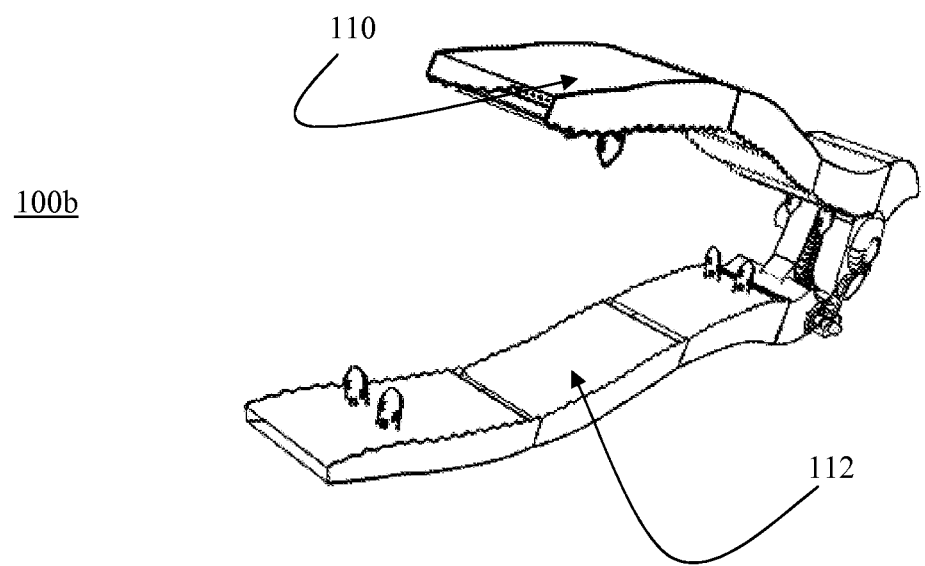
FIG. 3C illustrates a perspective (lateral oblique) view of the thoracic/lumbosacral TP staple in an open (unclamped) position, according to an exemplary embodiment of the invention.
Figure 3D:
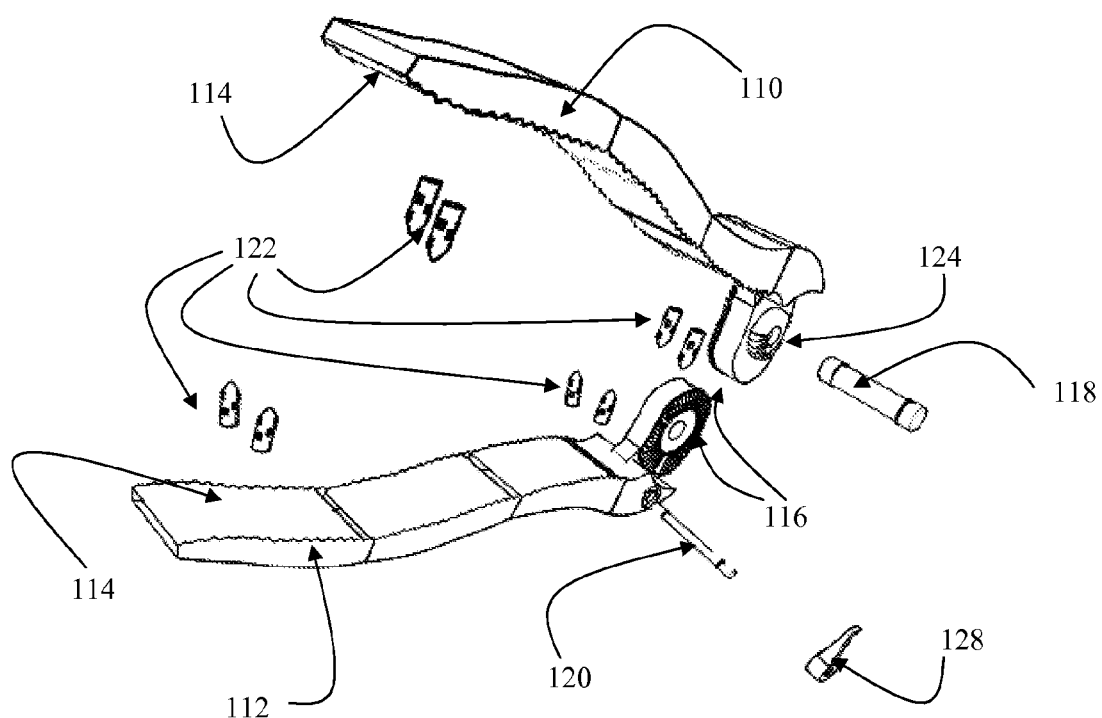
FIG. 3D illustrates an exploded view of the thoracic/lumbosacral TP staple, according to an exemplary embodiment of the invention.
Figure 4A:
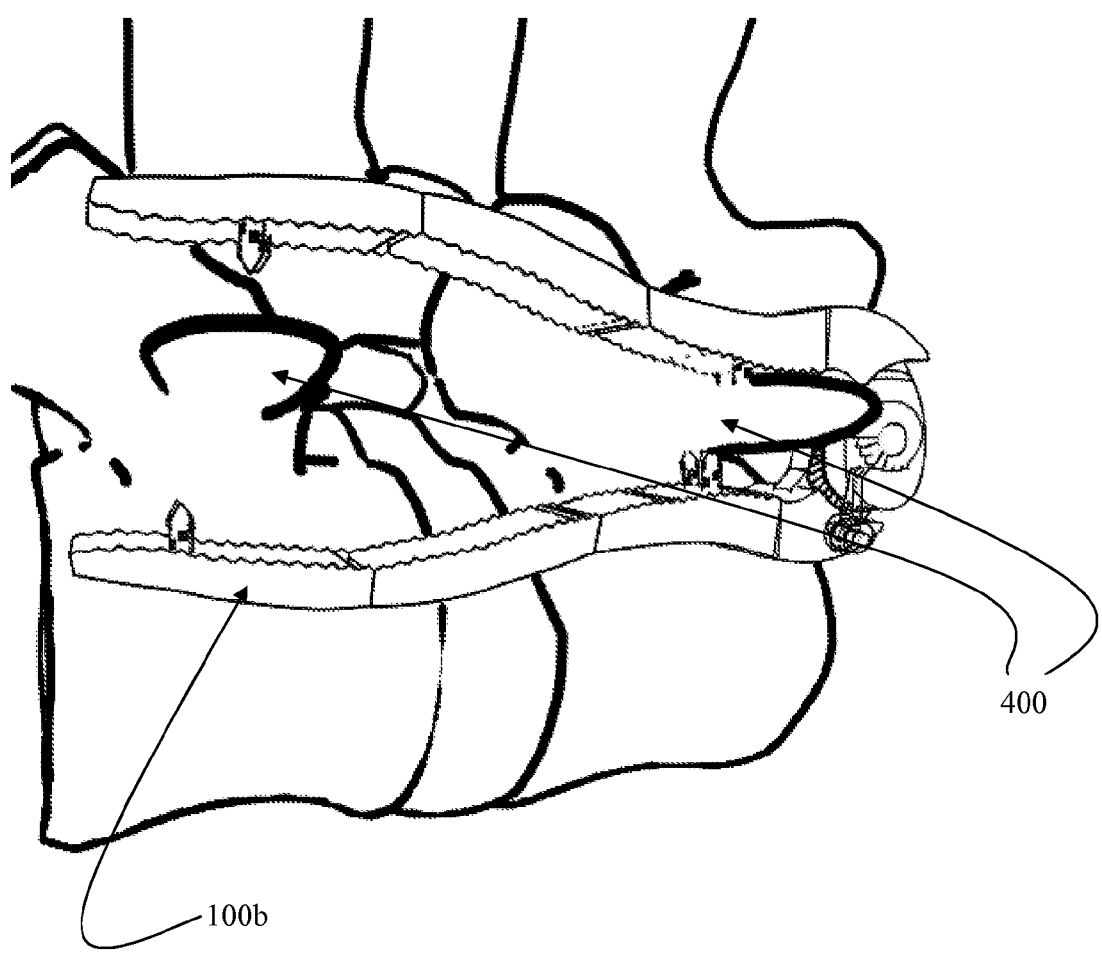
FIG. 4A illustrates a perspective (side oblique) assembly view of the lumbosacral Transverse Process (TP) staple articulating with two TPs in a partially open (partially clamped) position, according to an exemplary embodiment of the invention.
Figure 4B:
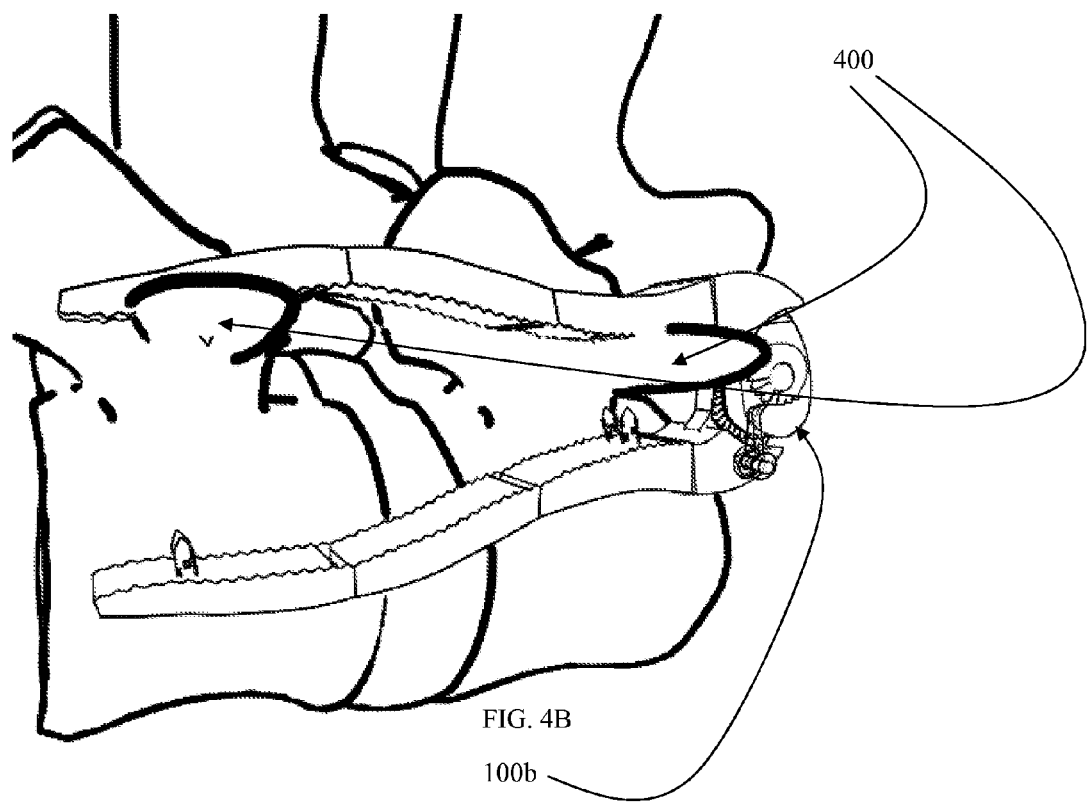
FIG. 4B illustrates a perspective (side oblique) assembly view of the lumbosacral TP staple articulating with two TPs in a partially open (partially clamped) position, according to an exemplary embodiment of the invention.
Figure 4C:
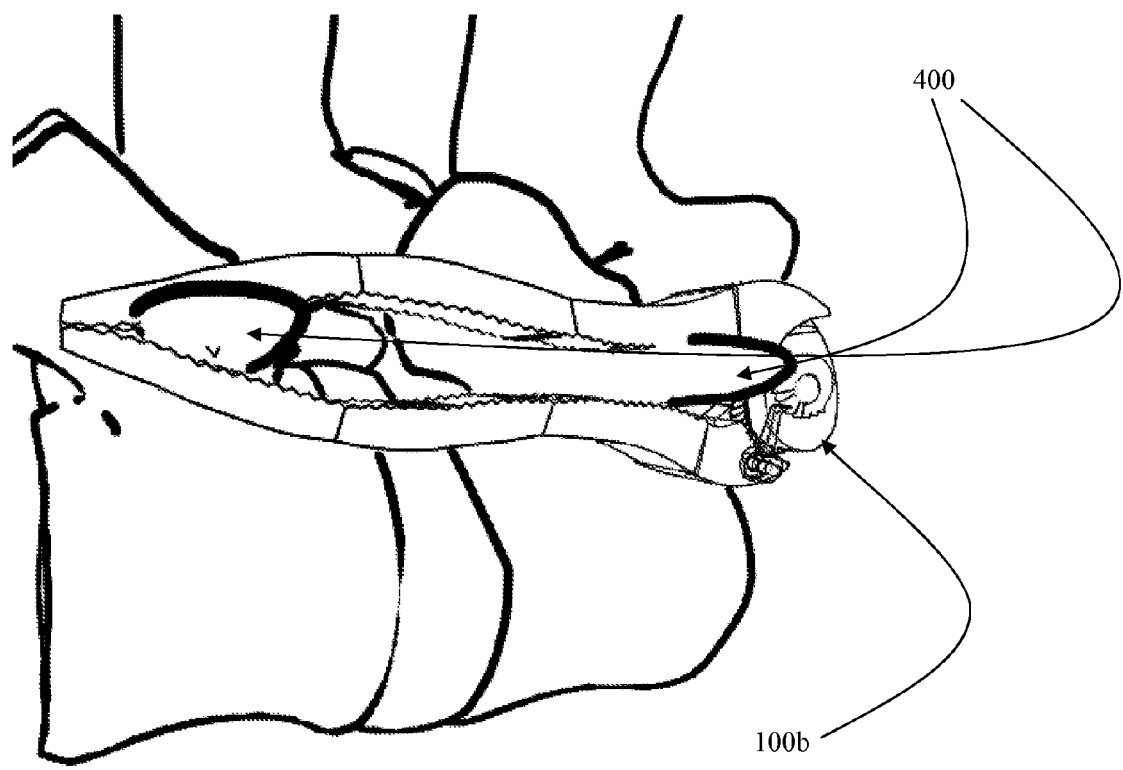
FIG. 4C illustrates a perspective (side oblique) assembly view of the lumbosacral TP staple articulating with two TPs in a closed (clamped) position, according to an exemplary embodiment of the invention.
Figure 4D:
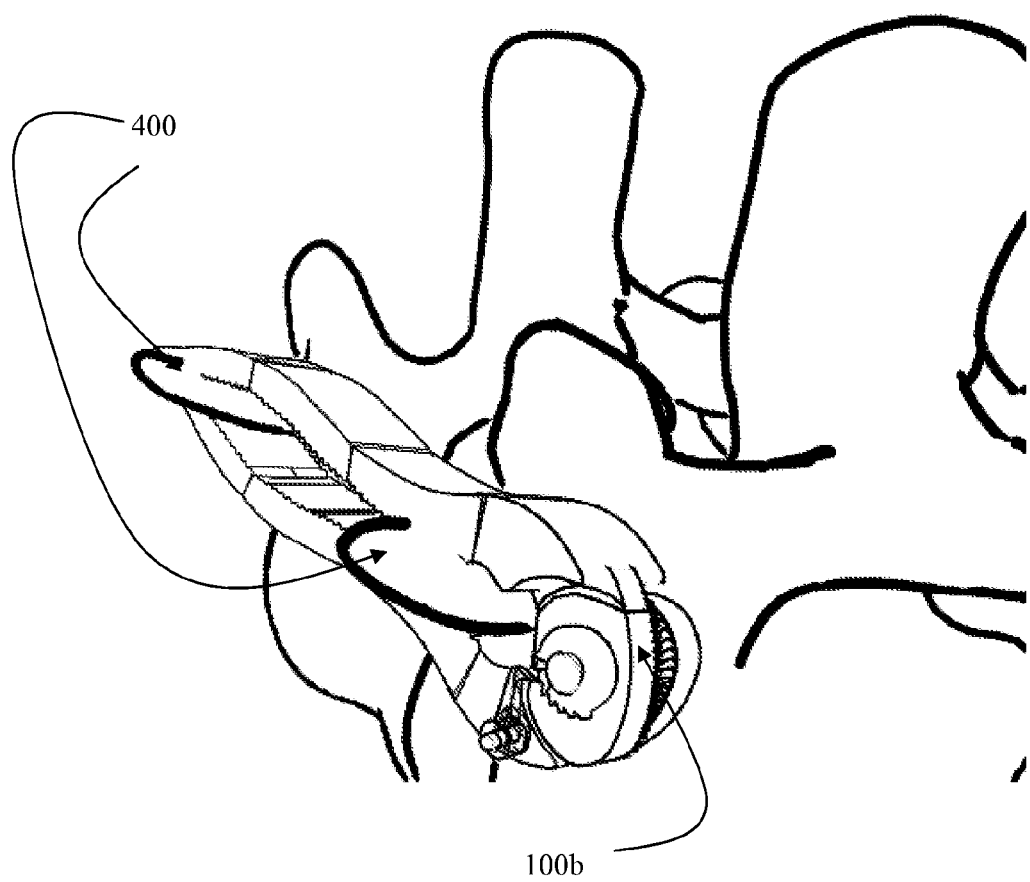
FIG. 4D illustrates a side perspective (posterior oblique) assembly view of the lumbosacral TP staple articulating with two TPs in a closed (clamped) position, according to an exemplary embodiment of the invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Alternate embodiments may be devised without departing from the scope of the invention. Additionally, well known elements of the invention will not be described in detail or will be omitted so as not to obscure the relevant details of the invention. The word "exemplary" is used herein to mean "serving as an example, instance, or illustration." Any embodiment described herein as "exemplary" is not necessarily to be construed as preferred or advantageous over other embodiments. Likewise the term "embodiments of the invention" does not require that all embodiments of the invention include the discussed feature, advantage or mode of operation.

With reference to FIGS. 1-9 exemplary embodiments of the invention will now be described.

1. Exemplary Medical Device

Referring to FIGS. 1-9, the above described problems of the conventional art can be solved in the thoracic, lumbar and cervical spines by insertions.

For example, FIGS. 1A-1D illustrate three dimensional views of an embodiment of the thoracic/lumbosacral Spinous Process (SP) staple apparatus 100a.

FIGS. 1A-1D illustrate an exemplary embodiment of a thoracic/lumbosacral SP staple 100a, for example, including a flexure spring (e.g., ratchet pawl 128). As shown in FIGS. 1A-1D, the features of the staple 100a can include top claws 110 and bottom claws 112 with claw ridges 114 to help incorporate and fuse with bone. A staple pin-pivot 118 can connect the top claws 110 and bottom claws 112. The staple 100a may include fastener pins/prongs 122 to help incorporate and fuse with bone; however, the staple 100a is not limited to any number of fastener pins/prongs 122. For example in the illustrated embodiments, the staple 100a includes sixteen fastener pins/prongs 122; eight per the top claw 110 and eight per the bottom claw 112. Further, a total of eight prongs 122 for engagement of two segmental SPs may be utilized such that each SP may be penetrated and perforated by a total of eight prongs 122; four prongs per single SP unit of penetration/engagement on the top claw 110 and four prongs per single SP unit of penetration/engagement on the bottom claw. However, in other embodiments, the staple 100a can include other amounts of fastener pins/prongs 122, such as four, six, eight, ten, etc. for engagement of the segmental SPs.

Claw teeth 116 may be molded onto the top claw 110 and bottom claw 112, and the claw teeth 116 may be interdigitating. Further, ratchet teeth 124 may be molded onto the bottom claw 112 (shown in FIGS. 1A-1B), and a ratchet pawl 128 (e.g., spring loaded ratchet pawl) may interact with the ratchet teeth 124 locking the staple 100a in position. The ratchet pawl 128 can be connected to the top claw 110 via ratchet bolt 120 and can rotate about the ratchet bolt 120 (shown in FIGS. 1A-1B).

In another embodiment, ratchet teeth 124 may also be molded on the top claw 110 (shown in FIGS. 1C-1D), and the ratchet pawl 128 may interact with the ratchet teeth 124 locking the staple 100a in position. The ratchet pawl 128 can be connected to the bottom claw 112 via ratchet bolt 120 and can rotate about the ratchet bolt 120 (shown in FIGS. 1C-1D).

As the staple 100a closes, the ratchet pawl 128 works in standard fashion. When a force is applied to open the staple 100a, the ratchet pawl 128 (e.g., a flexure spring) interacts with the ratchet teeth 124 exhibiting spring-like qualities due to its curvature resulting in the ratchet mechanism "locking up." Thus, the material used for the ratchet pawl 128 can contribute to the deformability and springiness of the ratchet mechanism, resulting in varying degrees of deformability and spring-like resistance. The ratchet mechanism can limit the opening force of the staple 100a by a force proportional to the stiffness of the ratchet pawl 128 (e.g., flexure spring). Further, the force can be tailored by making the ratchet pawl 128 from different materials or varying the dimension(s) of the ratchet pawl 128, or a flexure spring portion of the ratchet pawl 128. This embodiment can achieve significant rigidity (stiffness).

FIGS. 2A-2E illustrate a step-by-step mechanical engagement of an exemplary embodiment of a thoracic/lumbosacral Spinous Process (SP) staple 100a with two segmental SPs; beginning with the staple's fully opened position (FIG. 2A), then subsequently progressing to a semi-closed (partially clamped) position (FIG. 2B), and then subsequently and finally achieving a fully clamped position (FIGS. 2C-2E) entirely engaging and unifying the two segmental SPs.

FIGS. 3A-3D illustrate an exemplary embodiment of a thoracic/lumbosacral Transverse Process (TP) staple 100b.

As shown in FIGS. 3A-3D, the features of the staple 100b can include a top claw 110 and a bottom claw 112, each having claw ridges 114 to help incorporate and fuse with bone. A staple pin-pivot 118 can connect the top claw 110 and the bottom claw 112. The staple 100b may include fastener pins/prongs 122 to help incorporate and fuse with bone; however, the staple 100b is not limited to any number of fastener pins/prongs 122. For example in the illustrated embodiments, the staple 100b includes eight fastener pins/prongs 122; four per the top claw 110 and four per the bottom claw 112. Further, a total of four prongs 122 for engagement of two segmental TPs may be utilized such that each TP may be penetrated and perforated by a total of four prongs; two prongs per single TP unit of penetration/engagement on the top claw 110 and two prongs per single TP unit of penetration/engagement on the bottom claw 112. However, in other embodiments, the staple 100b can include other amounts of fastener pins/prongs 122, such as two, four, six, eight, ten, etc. for engagement of the segmental TPs.

Claw teeth 116 may be molded onto the top claw 110 and bottom claw 112, and the claw teeth 116 may be interdigitating. Further, ratchet teeth 124 may be molded on the top claw 110 (shown in FIGS. 3A-D), and the ratchet pawl 128 may interact with the ratchet teeth 124 locking the staple 100b in position. The ratchet pawl 128 can be connected to the bottom claw 112 via ratchet bolt 120 and can rotate about the ratchet bolt 120 (shown in FIGS. 3A-3D).

In another embodiment, ratchet teeth 124 may also be molded onto the bottom claw 112 (not shown), and a ratchet pawl 128 may interact with the ratchet teeth 124 locking the staple 100b in position. In this embodiment, the ratchet pawl 128 can be connected to the top claw 110 via ratchet bolt 120 and can rotate about the ratchet bolt 120 (not shown).

As the staple 100b closes, the ratchet pawl 128 works in standard fashion. When a force is applied to open the staple 100b, the ratchet pawl 128 (e.g., a flexure spring) interacts with the ratchet teeth 124 exhibiting spring-like qualities due to its curvature resulting in the ratchet mechanism "locking up." Thus, the material used for the ratchet pawl 128 can contribute to the deformability and springiness of the ratchet mechanism, resulting in varying degrees of deformability and spring-like resistance. The ratchet mechanism can limit the opening force of the staple 100b by a force proportional to the stiffness of the ratchet pawl 128 (e.g., flexure spring). Further, the force can be tailored by making the ratchet pawl 128 from different materials or varying the dimension(s) of the ratchet pawl 128, or a flexure spring portion of the ratchet pawl 128. This embodiment can achieve significant rigidity (stiffness).

FIGS. 4A-4D illustrate a step-by-step mechanical engagement of an exemplary embodiment of a thoracic/lumbosacral Transverse Process (TP) staple 100b with two segmental TPs; beginning with the staple's fully opened position (FIG. 4A), then subsequently progressing to a semi-closed position (partially clamped) (FIG. 4B), and then subsequently and finally achieving a fully clamped position (FIGS. 4C-4D) entirely engaging and unifying the two segmental TPs.

Figure 5:
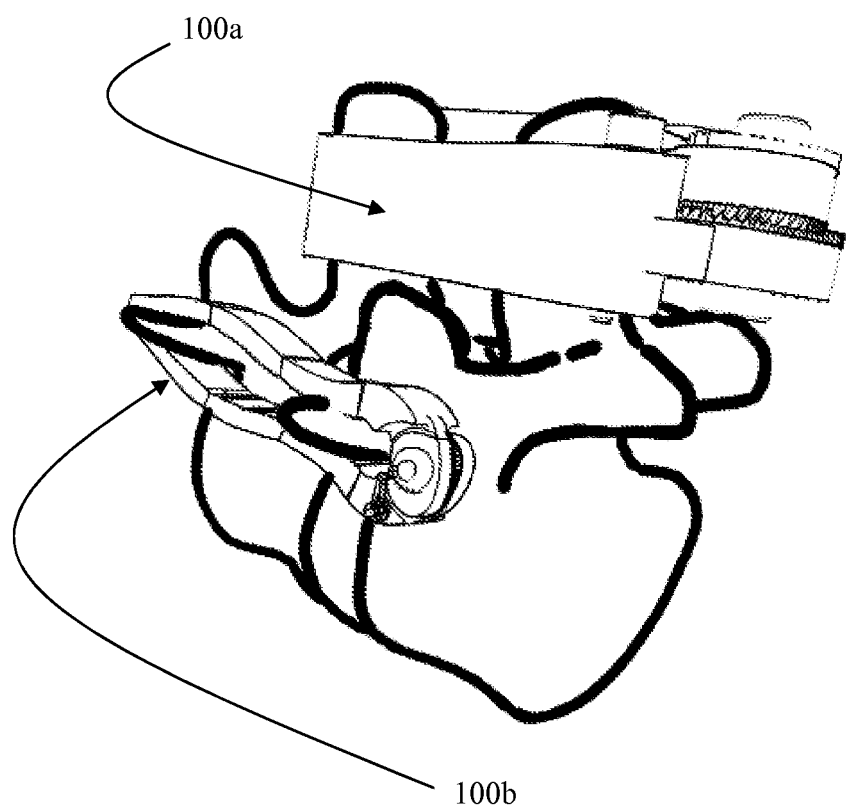
FIG. 5 illustrates a side perspective (posterior-oblique) assembly view of the thoracic/lumbosacral Spinous Process (SP) and Transverse Process (TP) staples engaging (clamped position) SPs and TPs of two adjacent spinal units, according to an exemplary embodiment of the invention.

FIG. 5 illustrates an exemplary embodiment of both a fully clamped thoracic/lumbosacral SP staple 100a and a fully clamped thoracic/lumbosacral TP staple 100b used to concomitantly staple/fuse two segmental spinal units.

Figure 6A:
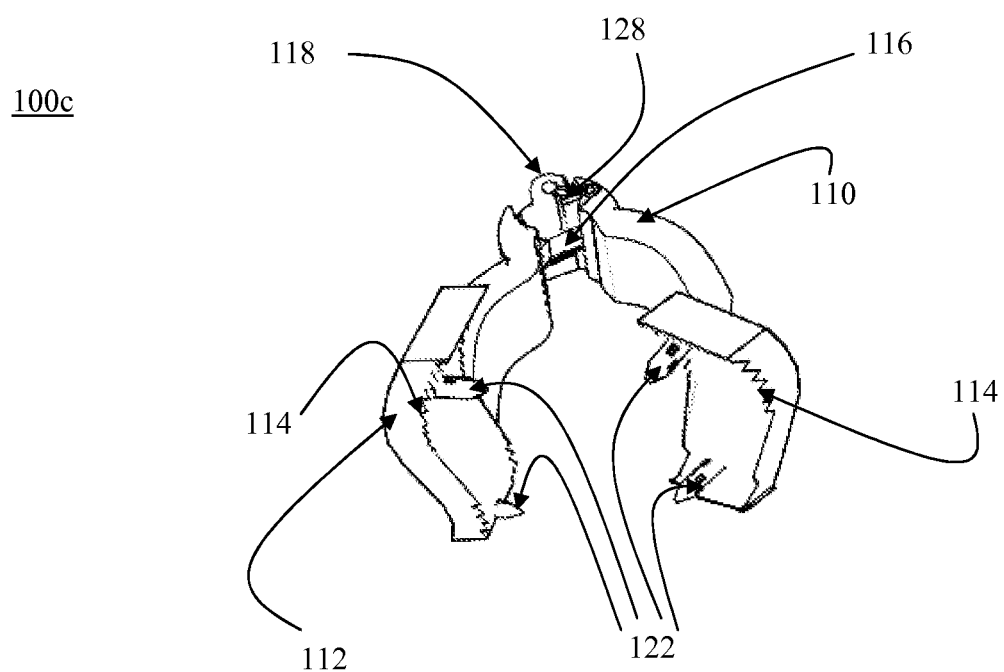
FIG. 6A illustrates a side perspective (top oblique) view of the cervical Spinous Process (SP) staple in a partially open (partially clamped) position, according to an exemplary embodiment of the invention.
Figure 6B:
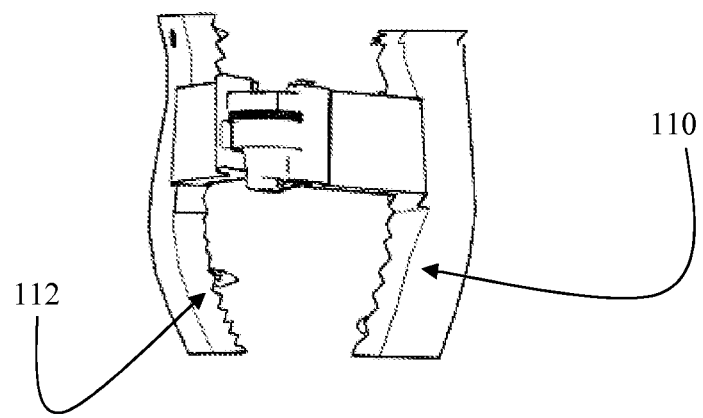
FIG. 6B illustrates a side perspective view of the cervical SP staple in a partially open (partially clamped) position, according to an exemplary embodiment of the invention.
Figure 6C:
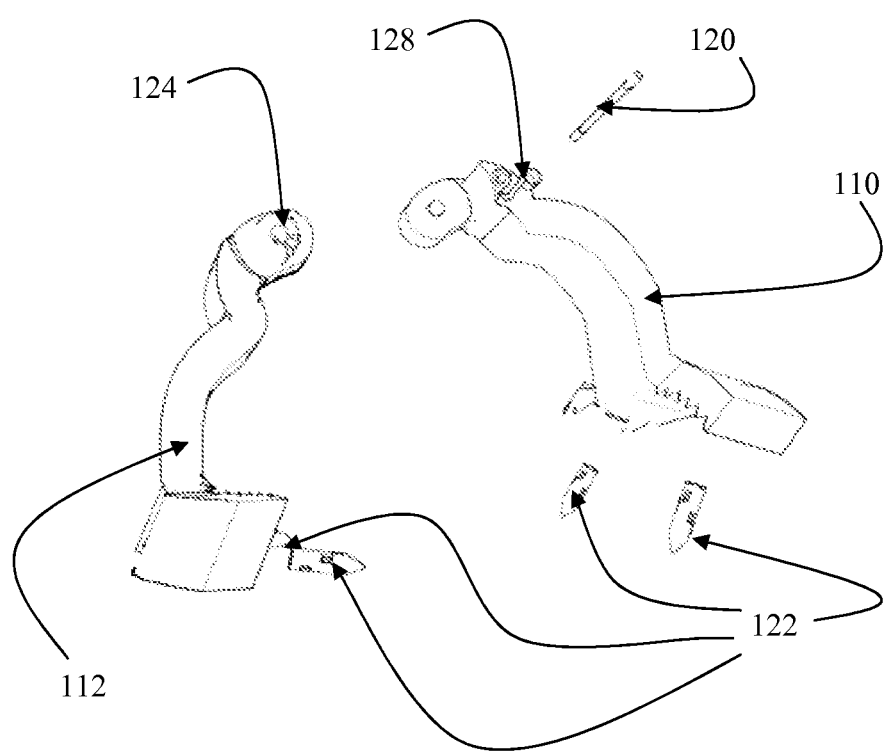
FIG. 6C illustrates an exploded view of the cervical SP staple, according to an exemplary embodiment of the invention.
Figure 7A:
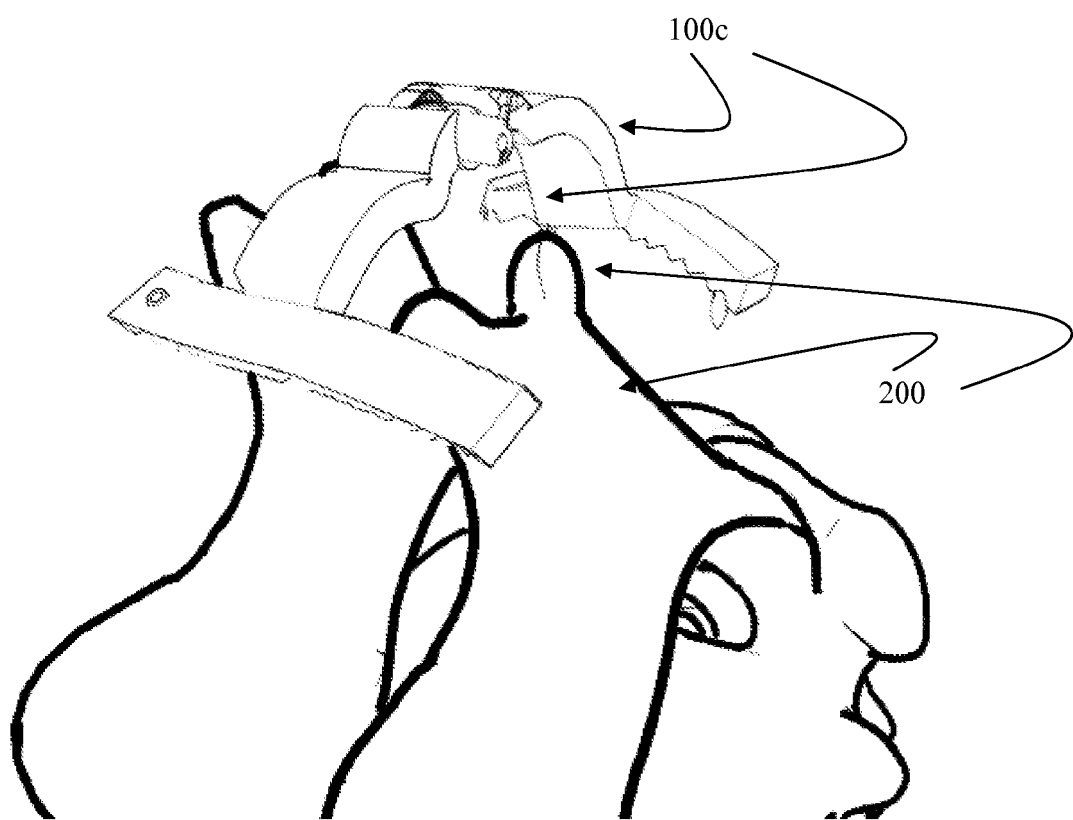
FIG. 7A illustrates a top perspective (side-oblique) assembly view of the cervical SP staple articulating with two SPs in a wide open position, according to an exemplary embodiment of the invention.
Figure 7B:
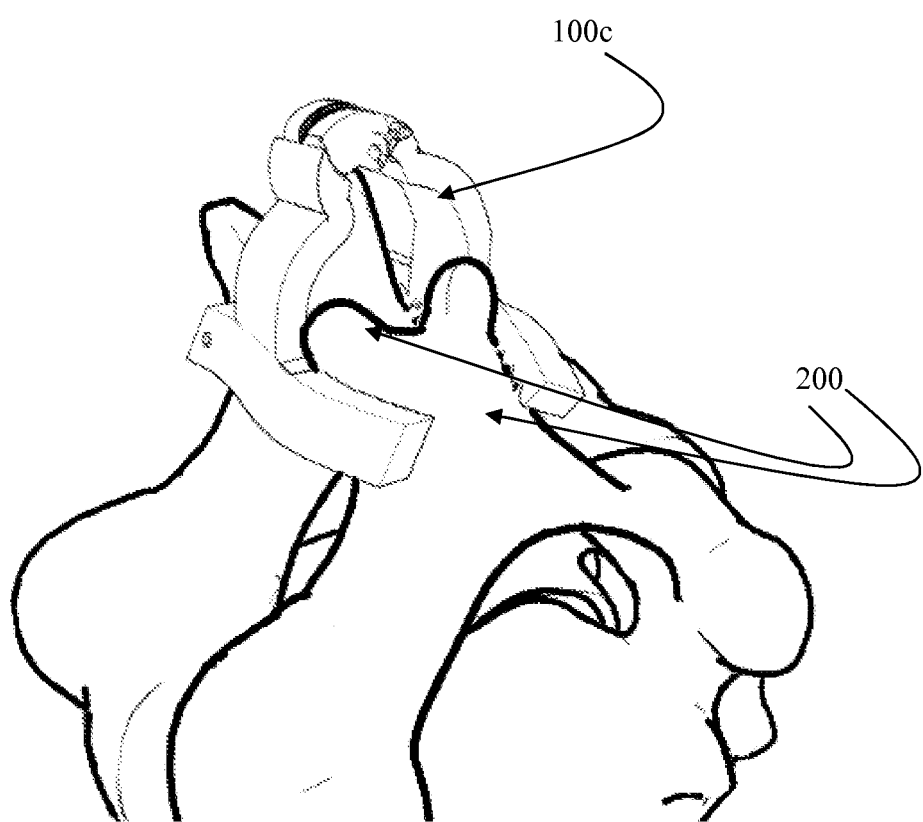
FIG. 7B illustrates a top perspective (top oblique) assembly view of the cervical SP staple articulating with two SPs in a closed (clamped) position, according to an exemplary embodiment of the invention.
Figure 7C:
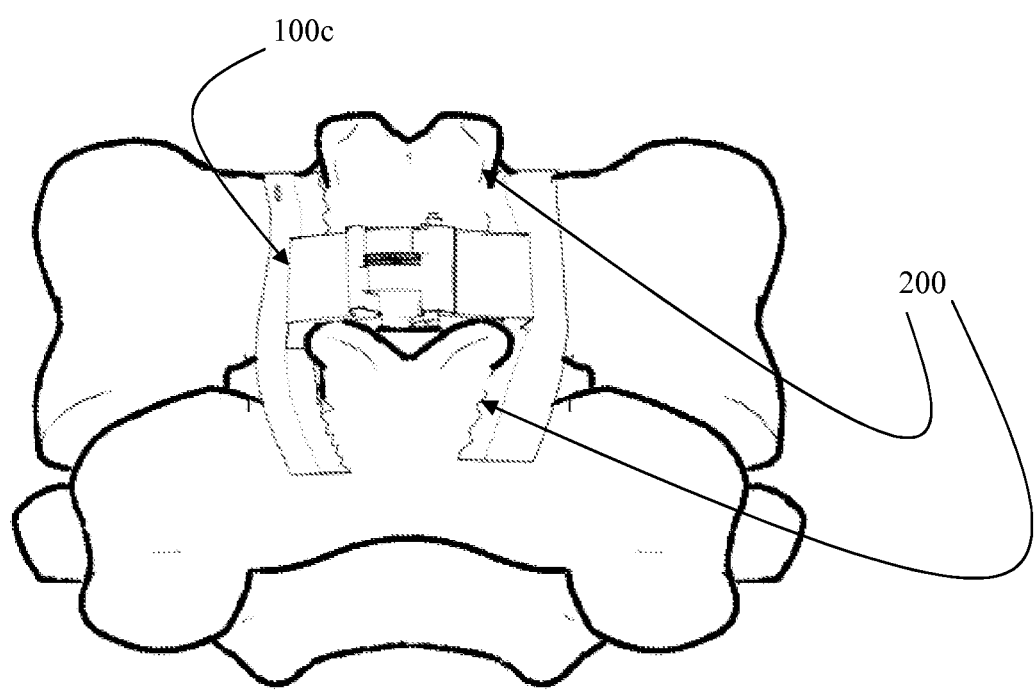
FIG. 7C illustrates a side assembly view of the cervical SP staple articulating with two SPs in a closed (clamped) position, according to an exemplary embodiment of the invention.
Figure 7D:
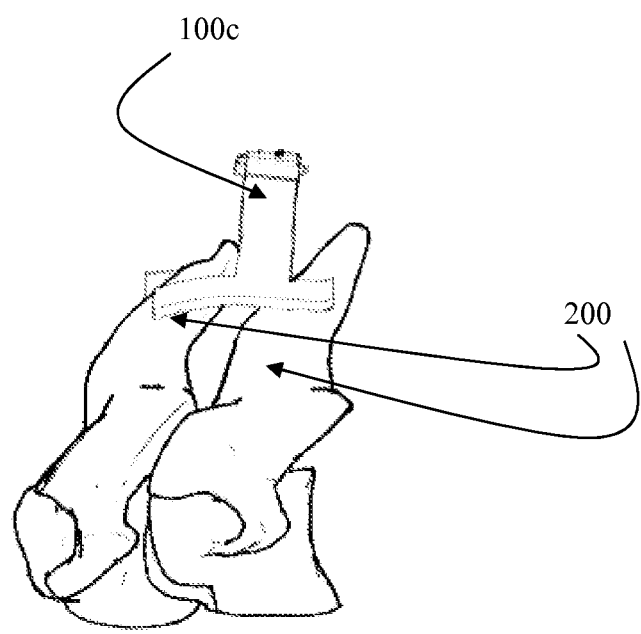
FIG. 7D illustrates a bottom assembly view of the cervical SP staple articulating with two SPs in a closed (clamped) position, according to an exemplary embodiment of the invention.

FIGS. 6A-6C illustrate an exemplary embodiment of a cervical Spinous Process (SP) staple 100c.

As shown in FIGS. 6A-6C, the features of the staple 100c can include a top claw 110 and a bottom claw 112, each having claw ridges 114 to help incorporate and fuse with bone. A staple pin-pivot 118 can connect the top claw 110 and the bottom claw 112. The staple 100c may include fastener pins/prongs 122 to help incorporate and fuse with bone; however, the staple 100c is not limited to any number of fastener pins/prongs 122. For example in the illustrated embodiments, the staple 100c includes four fastener pins/prongs 122; two per the top claw 110 and two per the bottom claw 112. Further, a total of two prongs 122 for engagement of each SP may be utilized such that each SP may be penetrated and perforated by a total of two prongs 122; one prong per single SP unit of penetration/engagement on the top claw 110 and one prong per single SP unit of penetration/engagement on the bottom claw 112. However, in other embodiments, the staple 100c can include other amounts of fastener pins/prongs 122, such as six, eight, ten, etc. for engagement of the cervical SPs.

Claw teeth 116 may be molded onto the top claw 110 and the bottom claw 112, and the claw teeth 116 may be interdigitating. Further, ratchet teeth 124 may be molded onto the bottom claw 112 (shown in FIGS. 6A-6C), and a ratchet pawl 128 may interact with the ratchet teeth 124 locking the staple 100c in position. The ratchet pawl 128 can be connected to the top claw 110 via ratchet bolt 120 and can rotate about the ratchet bolt 120 (shown in FIGS. 6A-6C).

In another embodiment, ratchet teeth 124 may also be molded on the top claw 110 (not shown), and the ratchet pawl 128 may interact with the ratchet teeth 124 locking the staple 100c in position. The ratchet pawl 128 can be connected to the bottom claw 112 via ratchet bolt 120 and can rotate about the ratchet bolt 120 (not shown).

As the staple 100c closes, the ratchet pawl 128 works in standard fashion. When a force is applied to open the staple 100c, the ratchet pawl 128 (e.g., a flexure spring) interacts with the ratchet teeth 124 exhibiting spring-like qualities due to its curvature resulting in the ratchet mechanism "locking up." Thus, the material used for the ratchet pawl 128 can contribute to the deformability and springiness of the ratchet mechanism, resulting in varying degrees of deformability and spring-like resistance. The ratchet mechanism can limit the opening force of the staple 100c by a force proportional to the stiffness of the ratchet pawl 128 (e.g., flexure spring). Further, the force can be tailored by making the ratchet pawl 128 from different materials or varying the dimension(s) of the ratchet pawl 128, or a flexure spring portion of the ratchet pawl 128. This embodiment can achieve significant rigidity (stiffness).

FIGS. 7A-7E illustrate a step-by-step mechanical engagement of an exemplary embodiment of the cervical Spinous Process (SP) staple 100c with two segmental cervical SPs; beginning with the staple's fully opened position (FIG. 7A), and then subsequently progressing to a fully clamped position (FIGS. 7B-7D) entirely engaging and unifying the two cervical TPs.

FIGS. 8A-8D illustrate exemplary embodiments of a straight fastener solid prong 122a, a straight perforated fastener prong 122b, a curved fastener solid prong 122c, and a curved perforated fastener prong 122d.

Figures 9A, 9B:
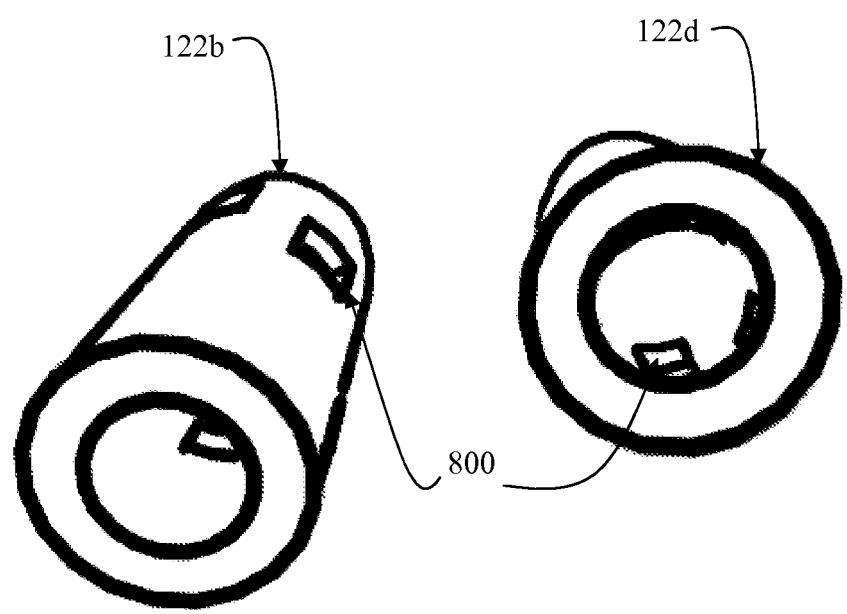
FIG. 9A illustrates a bottom perspective view of the straight-perforated staple prong, according to an exemplary embodiment of the invention.
FIG. 9B illustrates a bottom perspective view of the curved-perforated staple prong, according to an exemplary embodiment of the invention.

FIGS. 9A-9B illustrate a bottom perspective view of a straight-perforated staple prong 122b and a bottom perspective view of a curved-perforated staple prong 122d. The perforations 800 of these prongs allow insertion of bone and/or fusion material facilitating the fusion of the device to the spinous process thereby facilitating fusion. The perforations 800 can also be applied to other pins, staple screws involved in securing bone to facilitate fusion.

An exemplary embodiment of a thoracic/lumbar Spinous Process (SP) staple, can include first claw means (e.g., 110 or 112), second claw means (e.g., 110 or 112), a staple pin (e.g., 118) pivotally connecting the first claw means and the second claw means (e.g., 110, 112), and ratchet means (e.g., 124, 128) for limiting an opening force of the first claw means (e.g., 110 or 112) with respect to the second claw means (e.g., 110 or 112).

2. Exemplary Surgical Method

Exemplary surgical steps for practicing one or more of the foregoing exemplary embodiments will now be described.

Surgical implantation of the thoracic/lumbosacral Spinous Process (SP) staple (e.g., 100a) conjoining two adjacent SPs can be performed under standard open, closed, percutaneous, endoscopic, tubular, microscopic, fluoroscopic or any other standardized techniques. The staple (e.g., 100a) is applied to and engages with a staple gun (for example, as described in related application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11/536,815 filed on Sep. 29, 2006, and Ser. No. 11/208,644 filed on Aug. 23, 2005, which describe a facet joint (FJ) staple and staple gun). The staple gun can have a straight distal applier or angled applier to facilitate placement depending on the particular spinal anatomy. Upon exposure of two adjacent SP processes, the staple (e.g., 100a) is opened via the staple gun applier, the two adjacent SPs are engaged by the opened staple claws (e.g., 110, 112), and the staple gun then closes the upper and lower claws (e.g., 110, 112) which lead to the stapling/fusion of the two adjacent spinous processes (FIGS. 2A-2E). Depending on patient anatomy or surgical preference, the staple prongs (e.g., 122) can be either straight or curved. The staple prongs (e.g., 122) with perforations can be packed with any kind of bony/fusion material prior to placement on SPs. A variety of staples (e.g., 100a) with varying inter-prong distances to account for inter and intra-patient inter-spinous distance variations can be manufactured. The staple (e.g., 100a) with the correct approximate inter-spinous prong distance is selected.

Surgical implantation of the thoracic/lumbosacral Transverse Process (TP) staple (e.g., 100b) conjoining two adjacent TPs can be performed under standard open, closed, percutaneous, endoscopic, tubular, microscopic, fluoroscopic or any other standardized techniques. The Transverse Process (TP) staple (e.g., 100b) is applied to, and engages a staple gun (for example, as described in related application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11/536,815 filed on Sep. 29, 2006, and Ser. No. 11/208,644 filed on Aug. 23, 2005, which describe a facet joint (FJ) staple and staple gun). The staple gun can have a straight distal applier or angled applier to facilitate placement depending on the particular spinal anatomy. Upon exposure of the TP processes, the staple (e.g., 100b) is opened via the staple gun applier, the TPs are engaged by the opened staple claws (e.g., 110, 112), and the staple gun then closes the upper and lower claws (e.g., 110, 112) which lead to the stapling/fusion of two adjacent transverse processes (FIGS. 4A-4D). Depending on patient anatomy or surgical preference, the staple prongs (e.g., 122) can be either straight or curved. The staple prongs (e.g., 122) with perforations can be packed with any kind of bony/fusion material prior to placement on TPs. A variety of staples (e.g., 100b) with varying inter-prong distances to account for inter and intra patient inter TP distance variations can be manufactured. The staple (e.g., 100b) with the correct approximate inter TP prong distance is selected.

Surgical implantation of the cervical Spinous Process (SP) staple (e.g., 100c) can be performed under standard open, closed, percutaneous, endoscopic, tubular, microscopic, fluoroscopic or any other standardized techniques. The cervical Spinous Process (SP) staple (e.g., 100c) is applied to and engages a staple gun (for example, as described in related application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11/536,815 filed on Sep. 29, 2006, and Ser. No. 11/208,644 filed on Aug. 23, 2005, which describe a facet joint (FJ) staple and staple gun). The staple gun can have a straight distal applier or angled applier to facilitate placement depending on the particular spinal anatomy. Upon exposure of the cervical SP processes, the staple (e.g., 100c) is opened via the staple gun applier, the two adjacent cervical SPs are engaged from above by the opened staple claws (e.g., 110, 112), and the staple gun then closes the upper and lower claws (e.g., 110, 112) which lead to the stapling/fusion of cervical spinous processes (FIGS. 7A-7D). Depending on patient anatomy or surgical preference, the staple prongs (e.g., 122) can be either straight or curved. The staple prongs (e.g., 122) with perforations can be packed with any kind of bony/fusion material prior to placement on SPs. A variety of staples (e.g., 100c) with varying inter-prong distances to account for inter and intra patient inter-spinous distance variations can be manufactured. The staple (e.g., 100c) with the correct approximate inter-spinous prong distance is selected.

The present invention has been described herein in terms of several preferred embodiments. However, modifications and additions to these embodiments will become apparent to those of ordinary skill in the art upon a reading of the foregoing description. It is intended that all such modifications and additions comprise a part of the present invention to the extent that they fall within the scope of the several claims appended hereto.

What is claimed is:

1. An interarticulating staple for clamping one of a thoracic/lumbar Spinous Process (SP), a thoracic/lumbar Transverse Process (TP), and cervical Spinous Process (SP), the interarticulating staple comprising:
 a first claw;
 a second claw;
 a staple pin pivotally connecting the first claw and the second claw; and
 a ratchet mechanism that limits an opening force of the first claw with respect to the second claw at a fully open position, a fully closed position, and an intermediate position between the fully open position and the fully closed position.

2. The staple according to claim 1, wherein the ratchet mechanism comprises:
a ratchet pin pivotably mounted to the first claw,
wherein the second claw includes a plurality of ratchet teeth,
wherein the ratchet pin includes a flexure spring configured to sequentially engage individual teeth of the plurality of ratchet teeth as the first claw pivots about the staple pin with respect to the second claw in a closing direction, the flexure spring cooperating with each of the plurality of ratchet teeth to prevent an opening movement of the first claw with respect to the second claw in the opening direction at a plurality of positions including the fully open position, the fully closed position, and the intermediate position.

3. The staple according to claim 1, wherein the ratchet mechanism comprises:
a ratchet pin pivotably mounted to the second claw,
wherein the first claw includes a plurality of ratchet teeth,
wherein the ratchet pin includes a flexure spring configured to sequentially engage individual teeth of the plurality of ratchet teeth as the first claw pivots about the staple pin with respect to the second claw in a closing direction,
wherein, at each location where the flexure spring engages the individual teeth of the plurality of ratchet teeth, the flexure spring prevents the first claw from moving in an opening direction with respect to the second claw and permits the first claw to continue to move in the closing direction with respect to the second claw, and
wherein the flexure spring engages the individual teeth of the plurality of ratchet teeth at a plurality of positions including at least the fully open position, the fully closed position, and the intermediate position.

4. The staple according to claim 1, wherein the first claw includes a clamping surface and the second claw includes a clamping surface.

5. The staple according to claim 1, wherein the first claw includes a clamping surface having a plurality of ridges, and
wherein the second claw includes a clamping surface having a plurality of ridges.

6. The staple according to claim 1, wherein the first claw includes a clamping surface having a plurality of prongs.

7. The staple according to claim 6, wherein the second claw includes a clamping surface having a plurality of prongs.

8. The staple according to claim 6, wherein one of the plurality of prongs includes a perforation.

9. The staple according to claim 6, wherein one of the plurality of prongs includes a plurality of perforations.

10. The staple according to claim 6, wherein each of the plurality of prongs includes a perforation.

11. The staple according to claim 1, wherein the first claw and the second claw each include a portion having a staple pin opening,
wherein the portion having the staple pin opening of the first claw overlaps the portion having the staple pin opening of the second claw, and
wherein the staple pin engages the staple pin opening of the first claw and the second claw to pivotally connect the first claw to the second claw.

12. The staple according to claim 11, wherein the portion having the staple pin opening of each of the first claw and the second claw includes claw teeth, and
wherein the claw teeth of the first claw interdigitate with the claw teeth of the second claw.

13. The staple according to claim 4, wherein the clamping surface of the first claw opposes the clamping surface of the second claw.

14. The staple according to claim 2, wherein the ratchet pin is pivotably mounted to the first claw by a ratchet bolt.

15. The staple according to claim 1, wherein the ratchet mechanism comprises:
a ratchet pawl pivotably mounted to the first claw,
wherein the second claw includes a plurality of ratchet teeth, and
wherein a portion of the ratchet pawl is configured to sequentially engage individual teeth of the plurality of ratchet teeth to fix a position of the first claw with respect to the second claw at least at a fully open position, a fully closed position, and an intermediate position between the fully open position and the fully closed position.

16. The staple of claim 15, wherein of the ratchet pawl is configured to sequentially engage of the individual teeth of the plurality of ratchet teeth as the first claw pivots with respect to the second claw in a closing direction, and
wherein, at each location where the ratchet pawl engages the individual teeth of the plurality of ratchet teeth, the ratchet pawl prevents the first claw from moving in an opening direction with respect to the second claw and permits the first claw to continue to move in the closing direction with respect to the second claw.

17. The staple according to claim 2, wherein the ratchet pawl is pivotably mounted to the first claw by a ratchet bolt.

18. The staple according to claim 1, wherein the first claw includes a first clamping surface and the second claw includes a second clamping surface,
wherein the first clamping surface is opposed to the second clamping surface.

19. The staple according to claim 18, wherein each of the first clamping surface and the second clamping surface has a convex surface.

20. The staple according to claim 18, wherein each of the first clamping surface and the second clamping surface has a concave surface.

21. The staple according to claim 18, wherein the staple is a thoracic/lumbar Spinous Process (SP) staple configured to clamp a thoracic/lumbar Spinous Process (SP), and
wherein each of the first clamping surface and the second clamping surface has a concave surface.

22. The staple according to claim 6, wherein the staple is a thoracic/lumbar Spinous Process (SP) staple configured to clamp a thoracic/lumbar Spinous Process (SP),
wherein the plurality of prongs on the first claw are separated into a first group of prongs and a second group of prongs, and
wherein the first group of prongs on the first claw is separated from the second group of prongs on the first claw by a first distance that is substantially equal to an inter-lumbar Spinous Process (SP) distance.

23. The staple according to claim 7, wherein the staple is a thoracic/lumbar Spinous Process (SP) staple configured to clamp a thoracic/lumbar Spinous Process (SP),
wherein the plurality of prongs on the second claw are separated into a first group of prongs and a second group of prongs, and
wherein the first group of prongs on the second claw is separated from the second group of prongs on the second claw by a second distance that is substantially equal to an inter-lumbar Spinous Process (SP) distance.

24. The staple according to claim 7, wherein the staple is a thoracic/lumbar Spinous Process (SP) staple configured to clamp a thoracic/lumbar Spinous Process (SP),
wherein the plurality of prongs on the first claw are separated into a first group of prongs and a second group of prongs, wherein the first group of prongs on the first claw is separated from the second group of prongs on the first claw by a first distance that is substantially equal to an inter-lumbar Spinous Process (SP) distance, wherein the plurality of prongs on the second claw are separated into a first group of prongs and a second group of prongs, and wherein the first group of prongs on the second claw is separated from the second group of prongs on the second claw by a second distance that is substantially equal to the inter-lumbar Spinous Process (SP) distance.

25. The staple according to claim 24, wherein the first distance is equal to the second distance.

26. The staple according to claim 24, wherein the first distance is not equal to from the second distance.

27. The staple according to claim 18, wherein the staple is a thoracic/lumbar Transverse Process (TP) staple, and
wherein each of the first clamping surface and the second clamping surface has a concave surface portion.

28. The staple according to claim 18, wherein the staple is a thoracic/lumbar Transverse Process (TP) staple, and
wherein each of the first clamping surface and the second clamping surface has a convex surface portion and a concave surface portion.

29. The staple according to claim 18, wherein the staple is a thoracic/lumbar Transverse Process (TP) staple, and
wherein each of the first clamping surface and the second clamping surface has a convex surface portion and a concave surface portion,
wherein the convex surface portion of the first clamping surface of the first claw is opposed to the convex surface portion of the second clamping surface of the second claw, and
wherein the concave surface portion of the first clamping surface of the first claw is opposed to the concave surface portion of the second clamping surface of the second claw.

30. The staple according to claim 6, wherein the staple is a thoracic/lumbar Transverse Process (TP) staple configured to clamp a thoracic/lumbar Transverse Process (TP),
wherein the plurality of prongs on the first claw are separated into a first group of prongs and a second group of prongs, and
wherein the first group of prongs on the first claw is separated from the second group of prongs on the first claw by a first distance that is substantially equal to an inter-lumbar Transverse Process (TP) distance.

31. The staple according to claim 7, wherein the staple is a thoracic/lumbar Transverse Process (TP) staple configured to clamp a thoracic/lumbar Transverse Process (TP),
wherein the plurality of prongs on the second claw are separated into a first group of prongs and a second group of prongs, and
wherein the first group of prongs on the second claw is separated from the second group of prongs on the second claw by a second distance that is substantially equal to an inter-lumbar Transverse Process (TP) distance.

32. The staple according to claim 7, wherein the staple is a thoracic/lumbar Transverse Process (TP) staple configured to clamp a thoracic/lumbar Transverse Process (TP),
wherein the plurality of prongs on the first claw are separated into a first group of prongs and a second group of prongs,
wherein the first group of prongs on the first claw is separated from the second group of prongs on the first claw by a first distance that is substantially equal to an inter-lumbar Transverse Process (TP) distance,
wherein the plurality of prongs on the second claw are separated into a first group of prongs and a second group of prongs, and
wherein the first group of prongs on the second claw is separated from the second group of prongs on the second claw by a second distance that is substantially equal to the inter-lumbar Transverse Process (TP) distance.

33. The staple according to claim 32, wherein the first distance is equal to the second distance.

34. The staple according to claim 32, wherein the first distance is not equal to from the second distance.

35. The staple according to claim 18, wherein the staple is a cervical Spinous Process (SP) staple, and
wherein each of the first clamping surface and the second clamping surface has a concave surface portion.

36. The staple according to claim 18, wherein the staple is a cervical Spinous Process (SP) staple, and
wherein each of the first clamping surface and the second clamping surface has a convex surface portion and a concave surface portion.

37. The staple according to claim 18, wherein the staple is a cervical Spinous Process (SP) staple, and
wherein each of the first clamping surface and the second clamping surface has a convex surface portion and a concave surface portion,
wherein the convex surface portion of the first clamping surface of the first claw is opposed to the convex surface portion of the second clamping surface of the second claw, and
wherein the concave surface portion of the first clamping surface of the first claw is opposed to the concave surface portion of the second clamping surface of the second claw.

38. The staple according to claim 6, wherein the staple is a cervical Spinous Process (SP) staple configured to clamp a cervical Spinous Process (SP),
wherein the plurality of prongs on the first claw are separated into a first group of prongs and a second group of prongs, and
wherein the first group of prongs on the first claw is separated from the second group of prongs on the first claw by a first distance that is substantially equal to an inter-lumbar cervical Spinous Process (SP) distance.

39. The staple according to claim 7, wherein the staple is a cervical Spinous Process (SP) staple configured to clamp a cervical Spinous Process (SP),
wherein the plurality of prongs on the second claw are separated into a first group of prongs and a second group of prongs, and
wherein the first group of prongs on the second claw is separated from the second group of prongs on the second claw by a second distance that is substantially equal to an inter-lumbar cervical Spinous Process (SP) distance.

40. The staple according to claim 7, wherein the staple is a cervical Spinous Process (SP) staple configured to clamp a cervical Spinous Process (SP),
wherein the plurality of prongs on the first claw are separated into a first group of prongs and a second group of prongs,
wherein the first group of prongs on the first claw is separated from the second group of prongs on the first claw by a first distance that is substantially equal to an inter-lumbar cervical Spinous Process (SP) distance,
wherein the plurality of prongs on the second claw are separated into a first group of prongs and a second group of prongs, and wherein the first group of prongs on the second claw is separated from the second group of prongs on the second claw by a second distance that is substantially equal to the inter-lumbar cervical Spinous Process (SP) distance.

41. The staple according to claim 40, wherein the first distance is equal to the second distance.

42. The staple according to claim 40, wherein the first distance is not equal to the second distance.

43. The staple according to claim 6, wherein one of the plurality of prongs is a solid, straight prong.

44. The staple according to claim 6, wherein one of the plurality of prongs is a solid, curved prong.

45. The staple according to claim 6, wherein one of the plurality of prongs is a perforated, straight prong.

46. The staple according to claim 6, wherein one of the plurality of prongs is a perforated, curved prong.

47. The staple according to claim 8, wherein the perforation is configured to hold bone/biological fusion promoters to facilitate fusion.

48. An interarticulating staple for clamping one of a thoracic/lumbar Spinous Process (SP), a thoracic/lumbar Transverse Process (TP), and cervical Spinous Process (SP), the interarticulating staple comprising:
    first means for clawing bone;
    second means for clawing bone;
    a staple pin pivotally connecting the first means and the second means; and
    ratchet means for limiting an opening force of the first means with respect to the second means at a fully open position, a fully closed position, and an intermediate position between the fully open position and the fully closed position.

49. An interarticulating staple for clamping one of a thoracic/lumbar Spinous Process (SP), a thoracic/lumbar Transverse Process (TP), and cervical Spinous Process (SP), the interarticulating staple comprising:
    first means for clawing bone and second means for clawing bone, the first means pivotally connected to the second means; and
    ratchet means for limiting an opening force of the first means with respect to the second means and fixing a position of the first means with respect the second means at a fully open position, a fully closed position, and an intermediate position between the fully open position and the fully closed position.

50. An interarticulating staple for clamping one of a thoracic/lumbar Spinous Process (SP), a thoracic/lumbar Transverse Process (TP), and cervical Spinous Process (SP), the interarticulating staple comprising:
    a first claw having a first clamping surface and a second claw having a second clamping surface, wherein the first clamping surface and the second clamping surface cooperate to clamp a pair of adjacent spinous processes when the first claw and the second claw are in a closed position;
    a staple pin pivotally connecting the first claw and the second claw; and
    a ratchet mechanism that limits an opening force of the first claw with respect to the second claw at a fully open position, a fully closed position, and an intermediate position between the fully open position and the fully closed position.

51. A method of providing an interarticulating staple for positioning on a pair of adjacent spinous processes to clamp one of a thoracic/lumbar Spinous Process (SP), a thoracic/lumbar Transverse Process (TP), and cervical Spinous Process (SP), the method of providing the interarticulating staple comprising:
    providing a first claw having a first clamping surface and a second claw having a second clamping surface, wherein the first clamping surface and the second clamping surface cooperate to clamp the pair of adjacent spinous processes when the first claw and the second claw are in a closed position;
    providing a staple pin pivotally connecting the first claw and the second claw; and
    providing a ratchet mechanism that limits an opening force of the first claw with respect to the second claw at a fully open position, a fully closed position, and an intermediate position between the fully open position and the fully closed position such that the interarticulating staple can be secured to a pair of adjacent spinous processes by clamping the first clamping surface and the second clamping surface to the pair of adjacent spinous processes in at least one of the intermediate position and the fully closed position.

* * * * *